US007014890B2

(12) United States Patent
Bremer et al.

(10) Patent No.: US 7,014,890 B2
(45) Date of Patent: Mar. 21, 2006

(54) FLUORINATED NAPHTHALENES, LIQUID-CRYSTAL MIXTURES COMPRISING THEM, AND LIQUID-CRYSTAL DISPLAYS

(75) Inventors: Matthias Bremer, Darmstadt (DE); Melanie Klasen-Memmer, Heuchelheim (DE); Barbara Hornung, Hasselroth (DE); Wolfgang Schmidt, Dreieich (DE); Rainer Wingen, Hofheim (DE)

(73) Assignee: Merck Patent GmbH, Darmstadt (DE)

( * ) Notice: Subject to any disclaimer, the term of this patent is extended or adjusted under 35 U.S.C. 154(b) by 2 days.

(21) Appl. No.: 10/457,022

(22) Filed: Jun. 9, 2003

(65) Prior Publication Data
US 2004/0041125 A1 Mar. 4, 2004

(30) Foreign Application Priority Data
Jun. 7, 2002 (DE) .............................. 102 25 427

(51) Int. Cl.
C09K 19/32 (2006.01)
C09K 19/52 (2006.01)
C07C 23/18 (2006.01)
C07C 23/36 (2006.01)
C07C 25/22 (2006.01)

(52) U.S. Cl. ............ 428/1.1; 252/299.61; 252/299.62; 252/299.63; 252/299.66; 549/369; 570/183; 570/187; 570/188

(58) Field of Classification Search .................. 428/1.1; 252/299.61, 299.62, 299.63, 299.66; 570/183, 570/187, 188; 549/369
See application file for complete search history.

(56) References Cited

U.S. PATENT DOCUMENTS 6,159,392 A    12/2000  Schmidt et al.
6,159,561 A    12/2000  Schmidt et al.
6,455,744 B1 *  9/2002  Lal et al. .................... 570/143

FOREIGN PATENT DOCUMENTS

EP    0826659        5/1998
JP    2001-010995  * 1/2001

OTHER PUBLICATIONS

English translation by computer for JP 2001-010995, http://www4.ipdl.jpo.go.jp/Tokujitu/PAJdetail.ipdl?N0000=60&N0120=01&N2001=2&N3001=2001-010995.*
Adcock et al., "Substituent Effects. VIII. Synthesis of Substituted- alpha and beta-Fluoronaphthalenes", J. of Amercan Chemica Society, 1967, vol. 89, pp. 386-390.*
Chang et al., "Nitration of 2,3-dimethoxynaphthalene", J. Chem. Soc. section C, 1967, pp. 840-842.*
Gillespie et al., "Synthesis of Fagaronine. An Anticancer Benzophenanthridine Alkaloid", J. Org. Chme., vol. 39, No. 22, pp. 3239-3241, 1974.*

* cited by examiner

Primary Examiner—Shean C. Wu
(74) Attorney, Agent, or Firm—Millen, White, Zelano, Branigan, P.C.

(57) ABSTRACT

Compounds of the formula (I)

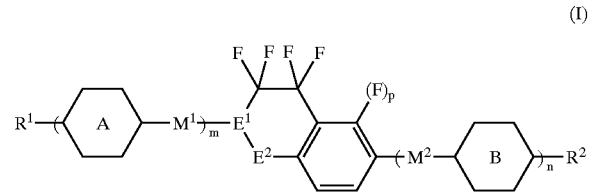

in which the parameters are as defined herein, are suitable for use in liquid-crystal media and liquid-crystal displays which contain these media.

34 Claims, No Drawings

FLUORINATED NAPHTHALENES, LIQUID-CRYSTAL MIXTURES COMPRISING THEM, AND LIQUID-CRYSTAL DISPLAYS

Fluorinated derivatives of naphthalene have been disclosed, for example in U.S. Pat. Nos. 6,159,392, 6,159,561 or Mol. Cryst. Liq. Cryst. 364, 865 (2001), for use in liquid-crystalline mixtures.

EP 0 826 659 discloses a general formula of compounds containing fluorinated dihydronaphthyl rings. However, this document describes neither specific compounds containing more than one fluorine atom in the dihydronaphthalene nor compounds in which the aromatic ring is fluorinated. However, the latter in particular are distinguished by particularly favourable dielectric properties.

Since, however, the development of liquid-crystal mixtures can in no way be regarded as complete, the manufacturers of displays are interested in a very wide variety of components for mixtures.

In particular, there is a need for liquid-crystal mixtures which firstly have a very broad working temperature range and secondly have the lowest possible threshold voltage, for example for use in automobiles, in which a temperature range of from −40° C. to 100° C. can easily occur, but also for portable equipment, such as mobile telephones and notebook PCs.

There is therefore an ongoing demand for novel, suitable liquid-crystal mixtures and mixture components.

An object of the present invention is therefore to provide novel components for use in nematic or cholesteric liquid-crystal mixtures which have high absolute values of the dielectric anisotropy of negative sign combined with a favourable ratio of viscosity and clearing point. In addition, the compounds should have high light, UV and thermal stability. They should furthermore be suitable for achieving a high voltage holding ratio (VHR). They should furthermore be readily accessible synthetically and therefore potentially inexpensively.

Upon further study of the specification and appended claims, further objects and advantages of this invention will become apparent to those skilled in the art.

It has now been found that these objects are achieved by the fluorinated naphthalenes of the formula (I)

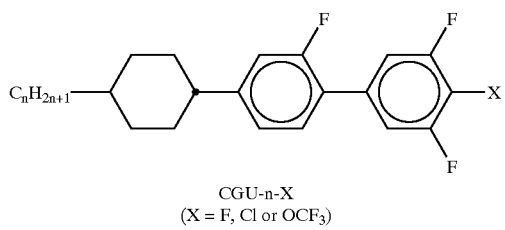

CGU-n-X
(X = F, Cl or OCF$_3$)

in which:
$R^1$ and $R^2$, independently of one another, are each H, a linear alkyl radical having from 1 to 12 carbon atoms or a linear or branched alkenyl radical having from 2 to 8 carbon atoms, in which, in addition,
  a) a (non-terminal) —CH$_2$— group may be replaced by —O— or —C(=O)O— and/or
  b) a —CH$_2$— group may be replaced by —C≡C—, cyclopropane-1,2-diyl or cyclobutane-1,3-diyl and/or
  c) a plurality of H may be replaced by F, with the proviso that $R^1$ and $R^2$ are not simultaneously H,
$M^1$ and $M^2$, independently of one another, are each —C(=O)O—, —OC(=O)—, —CH$_2$O—, —OCH$_2$—, —C≡C—, —CH$_2$CH$_2$—, —(CH$_2$)$_4$—, —CF$_2$CF$_2$—, —CF$_2$O—, —OCF$_2$— or a single bond,
>$E^1$-$E^2$- is the >C=CH— or >CH—CH$_2$— group,
m and n, independently of one another, are each zero, 1 or 2, with the proviso that the sum m+n is 0, 1 or 2,
p is zero or 1,

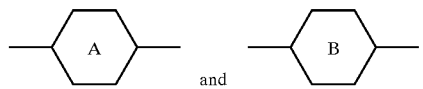

independently of one another, are each phenylene-1,4-diyl, optionally monosubstituted, disubstituted or trisubstituted by F, cyclohexane-1,4-diyl, optionally monosubstituted or disubstituted by F, 1-cyclohexene-1,4-diyl, optionally monosubstituted by F, or 1,3-dioxane-2,5-diyl.

Preference is given to the compounds of the formula (I) in which >$E^1$-$E^2$- is >C=CH—.

Preference is likewise given to the compounds of the formula (I) in which p=1.

Preference is likewise given to the compounds of the formula (I) in which m=1 or 2; n=0; $M^1$ and $M^2$=single bond.

Preference is likewise given to the compounds of the formula (I) in which m=0; n=1 or 2; $M^1$ and $M^2$=single bond.

Preference is likewise given to the compounds of the formula (I) in which m=1 or 2;

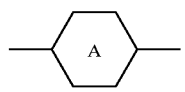

is phenylene-1,4-diyl or cyclohexane-1,4-diyl.
Preference is likewise given to the compounds of the formula (I) in which n=1 or 2,

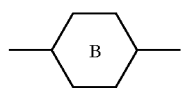

is phenylene-1,4-diyl or cyclohexane-1,4-diyl.
Particular preference is given to the compounds of the formula (I) in which $E^1$-$E^2$-=>C=CH—; p=1; m=1 or 2; n=0;

is phenylene-1,4-diyl or cyclohexane-1,4-diyl.
Particular preference is also given to the compounds of the formula (I) in which >$E^1$-$E^2$-=>C=CH—; p=1; m=0; n=1 or 2;

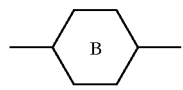

is phenylene-1,4-diyl or cyclohexane-1,4-diyl.

If one of $R^1$ and $R^2$ is an alkyl radical, it is preferably methyl, ethyl, propyl, butyl, pentyl, hexyl, heptyl, octyl, nonyl, decyl, undecyl, or dodecyl. If one of $R^1$ and $R^2$ is an alkyl radical in which a —$CH_2$— group is replaced by —O—, it is preferably an alkoxy such as ethoxy, propoxy, butoxy, pentoxy, hexyloxy, heptoxy, octoxy nonoxy, decoxy, undecoxy, or dodecoxy, or is oxaalkyl (alkxoyalkyl) such as 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-6- or 7-oxaoctyl, 2-, 3-, 4-, 5-, 6-, 7- or 8-oxanonyl or 2-, 3-, 4-, 5-, 6-, 7-, 8- or 9-oxadecyl.

Especial preference is given to the compounds of the formulae (Ia) to (Ij):

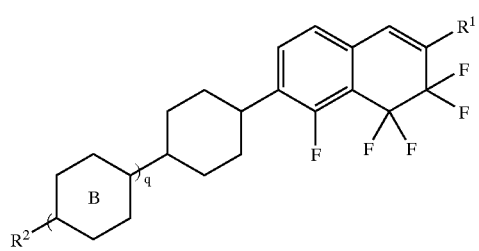

(Ia)

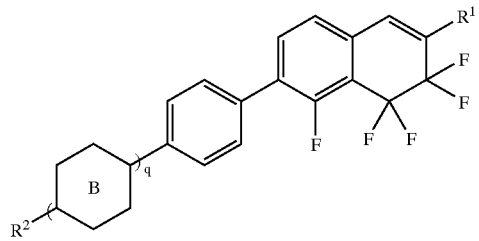

(Ib)

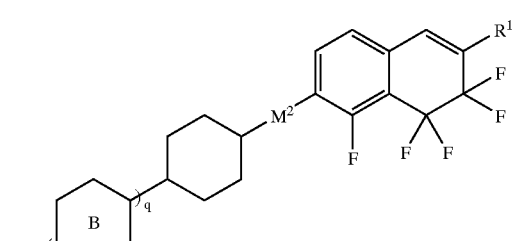

(Ic)

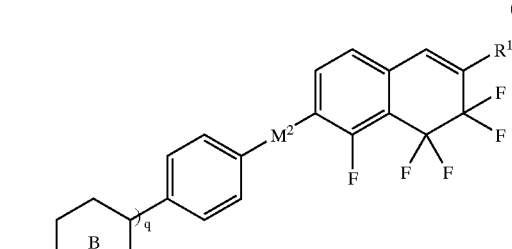

(Id)

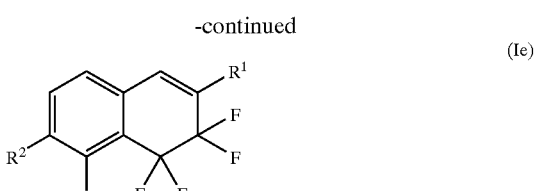

(Ie)

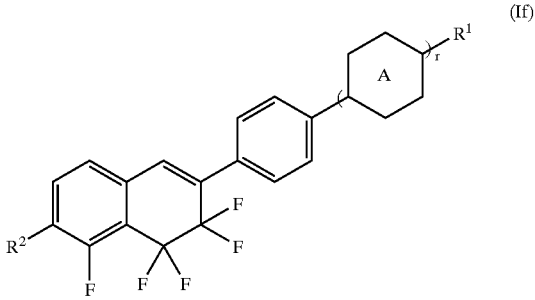

(If)

(Ig)

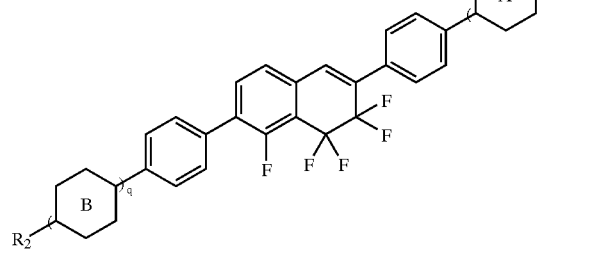

(Ih)

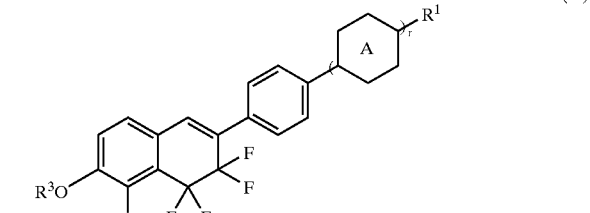

(Ii)

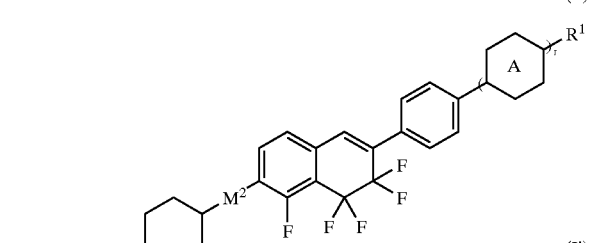

(Ij)

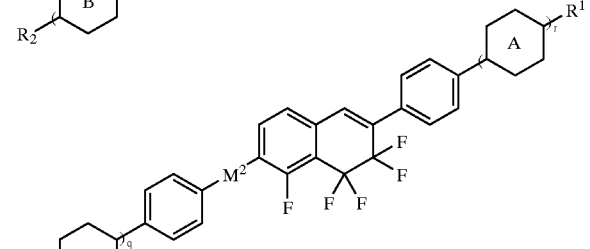
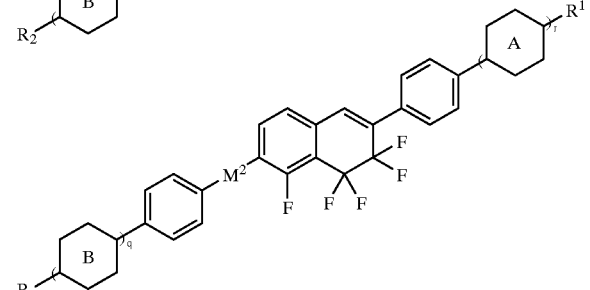

$R^3$ is an alkyl radical having from 1 to 12 carbon atoms or an alkenyl radical having from 2 to 8 carbon atoms.

q is 0 or 1.

r is 0 or 1, with the proviso that the sum q+r in the compounds of the formulae (Ig), (Ii) and (Ij) is 0 or 1.

Very especial preference is given to the compounds of the formulae

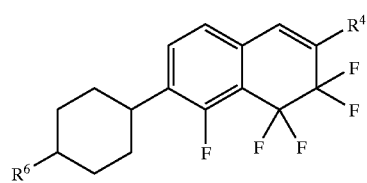
(Ia1)

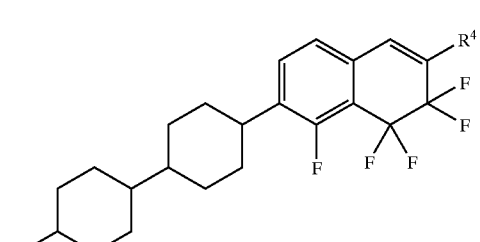
(Ia2)

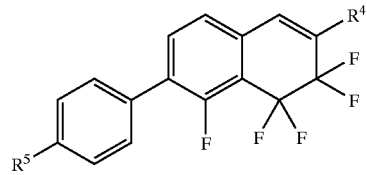
(Ib1)

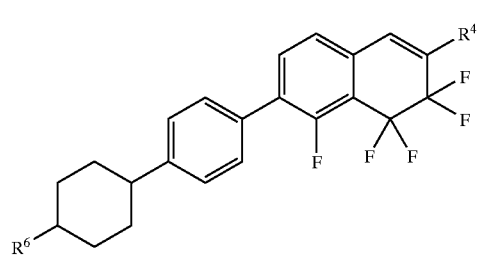
(Ib2)

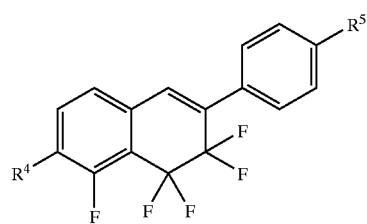
(If1)

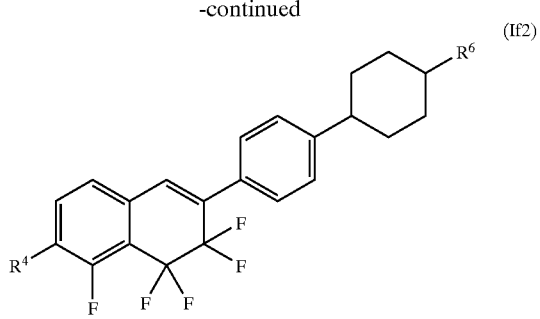
(If2)

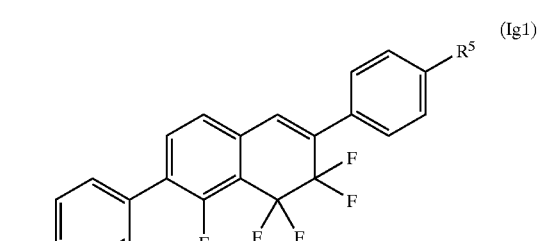
(Ig1)

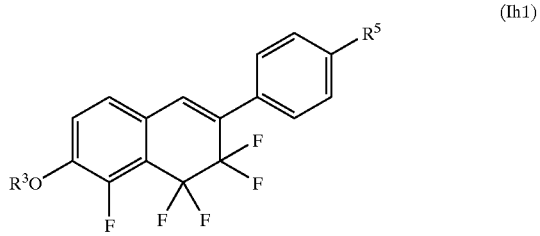
(Ih1)

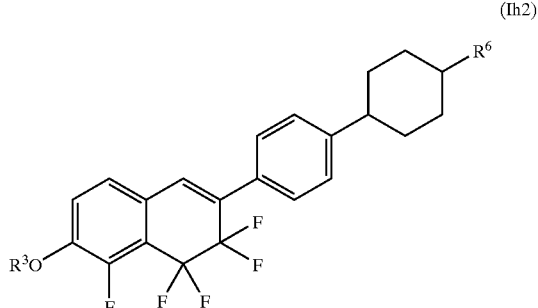
(Ih2)

$R^3$ is an alkyl radical having from 1 to 12 carbon atoms or an alkenyl radical having from 2 to 8 carbon atoms.

$R^4$ is an alkyl radical having from 1 to 6 carbon atoms or an alkenyl radical having from 2 to 6 carbon atoms, in each of which a (non-terminal) —CH$_2$— group may also be replaced by —O—.

$R^5$ is an alkyl radical having from 1 to 6 carbon atoms or an alkenyl radical having from 2 to 6 carbon atoms, in each of which a (non-terminal) —CH$_2$— group may also be replaced by —O—.

$R^6$ is an alkyl radical having from 1 to 6 carbon atoms.

Very generally, the provision of compounds of the formula (I) considerably broadens the range of liquid-crystalline substances which are suitable, from various applicational points of view, for the preparation of liquid-crystalline mixtures.

In this connection, the compounds of the formula (I) have a broad range of applications. Depending on the choice of substituents, they can be added to other classes of compound in order, for example, to modify the dielectric and/or optical anisotropy of a dielectric of this type. They may also serve to optimise its threshold voltage and/or its viscosity.

The compounds of the formula (I) are particularly suitable, even when added in small amounts, for modifying the dielectric anisotropy (Δε), in particular for achieving higher absolute values of the dielectric anisotropy of negative sign.

The invention thus relates to compounds of the formula (I) and to the use of these compounds as components of liquid-crystalline mixtures and liquid-crystal mixtures comprising compounds of the formula (I).

The compounds of the formula (I) are preferably employed in nematic or cholesteric liquid-crystal mixtures. The liquid-crystal mixtures according to the invention comprise at least one compound of the formula (I), preferably in an amount of from 1 to 80% by weight, particularly from 3 to 40% by weight, based on the liquid-crystal mixture. They preferably comprise at least 3 further compounds. The choice of these further compounds (for example from the types listed in DE-A-196 29 812, pp. 12 to 16) and the preparation of the liquid-crystal mixtures are familiar to the person skilled in the art.

The invention also relates to a liquid-crystal display which contains these liquid-crystal mixtures. This liquid-crystal display preferably operates in IPS display mode (Kiefer et al., Japan Display '92, p. 547) or in VA display mode (Ohmura et al., SID 97 Digest, p. 845) or in ECB display mode (EP-A-0 474 062).

The compounds of the formula (I) are likewise preferably employed in chiral smectic liquid-crystal mixtures. The liquid-crystal mixtures according to the invention comprise at least one compound of the formula (I), preferably in an amount of from 1 to 40% by weight, based on the liquid-crystal mixture. They preferably comprise at least 3 further components. These components are preferably selected from the known compounds having smectic and/or nematic and/or cholesteric phases. The choice of these further compounds (for example from the types listed in DE-A-198 57 352) and the preparation of the liquid-crystal mixtures are familiar to the person skilled in the art.

The invention also relates to a liquid-crystal display which contains these liquid-crystal mixtures.

The display elements (displays) according to the invention are usually constructed in such a way that a liquid-crystal layer is enclosed on both sides by layers which are usually, in this sequence starting from the LC layer, at least one alignment layer, electrodes and a limiting sheet (for example made of glass). In addition, they may contain spacers, adhesive frames, polarisers and, for colour displays, thin coloured filter layers. Further possible components are antireflection, passivation, compensation and barrier layers and electrically nonlinear elements, such as thin-film transistors (TFTs) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

The compounds according to the invention are particularly preferably used in displays of the AMD-TN, AMD-IPS or AMD-VA (also AMD-ECB) type.

Possible synthetic routes to compounds of the formula (I) are indicated by way of example in the following schemes, with other processes also being conceivable and possible.

The following abbreviations are used:

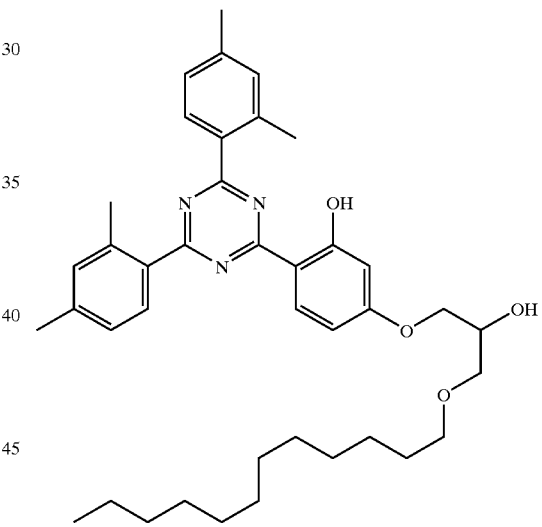

Scheme 1

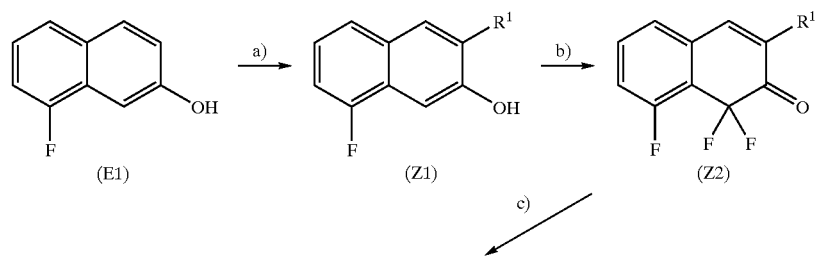

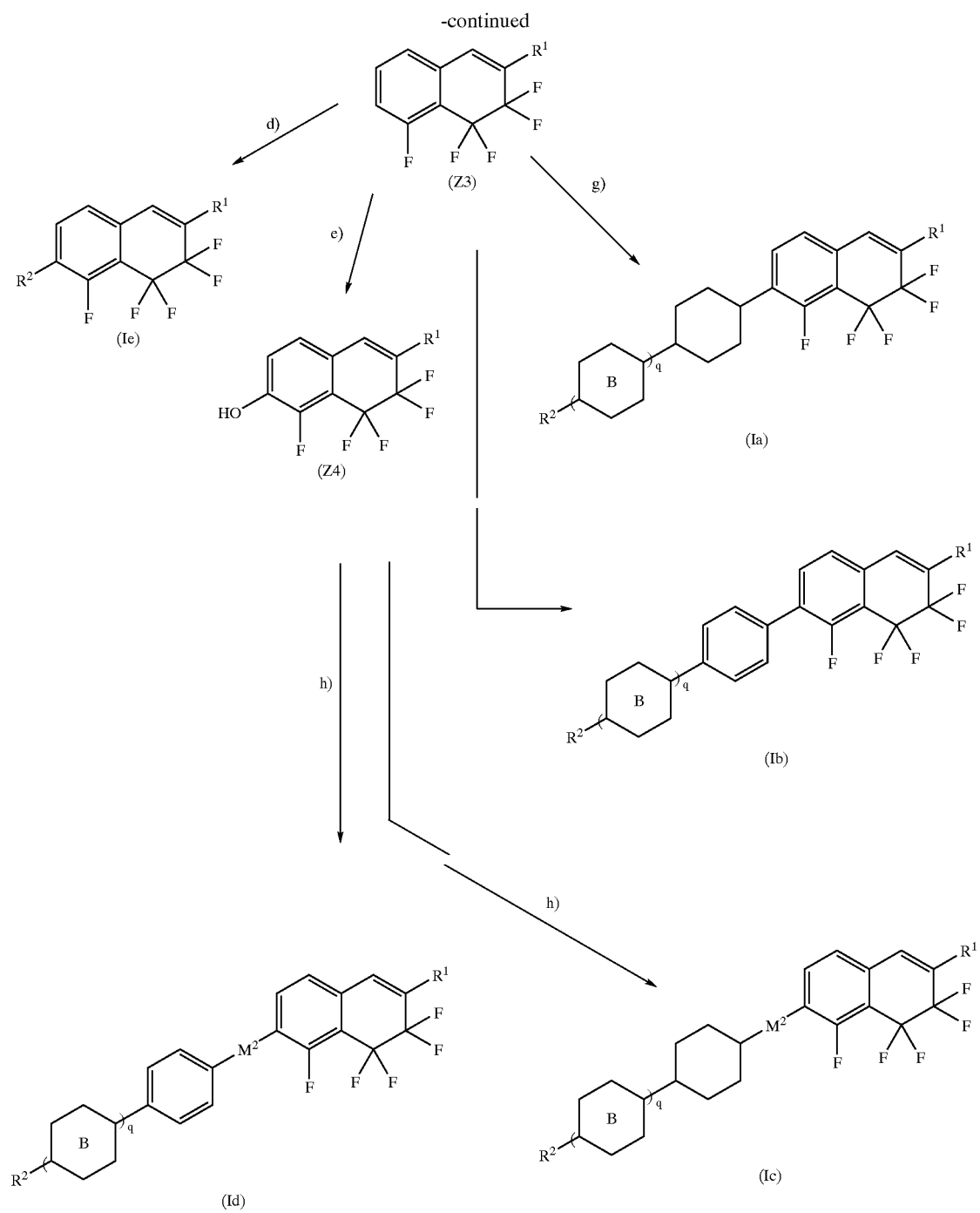
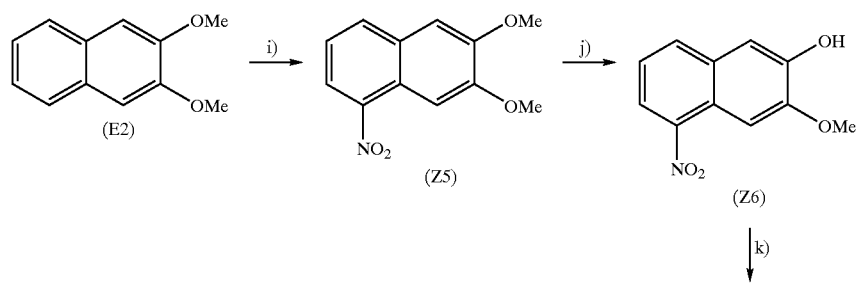

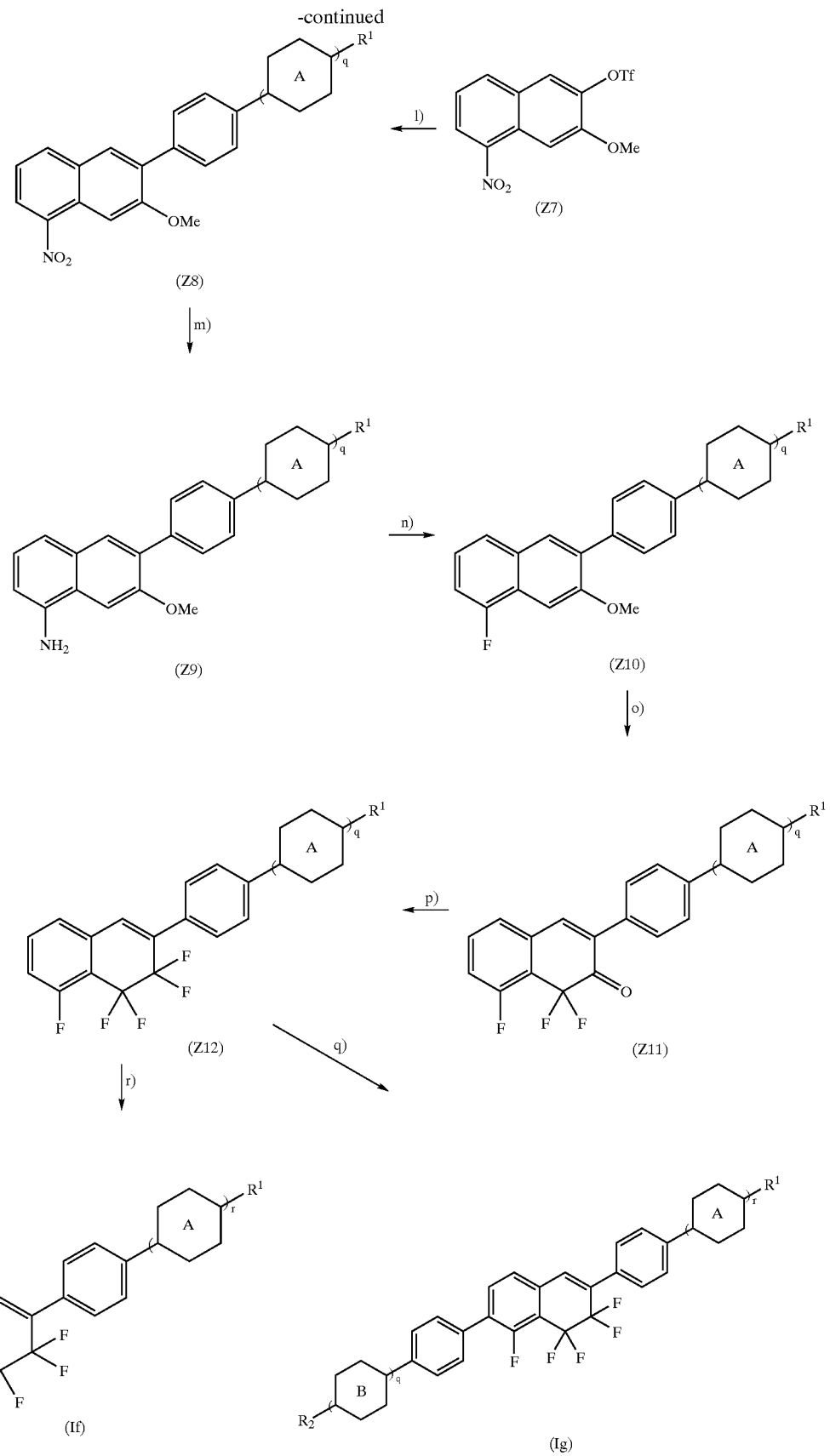

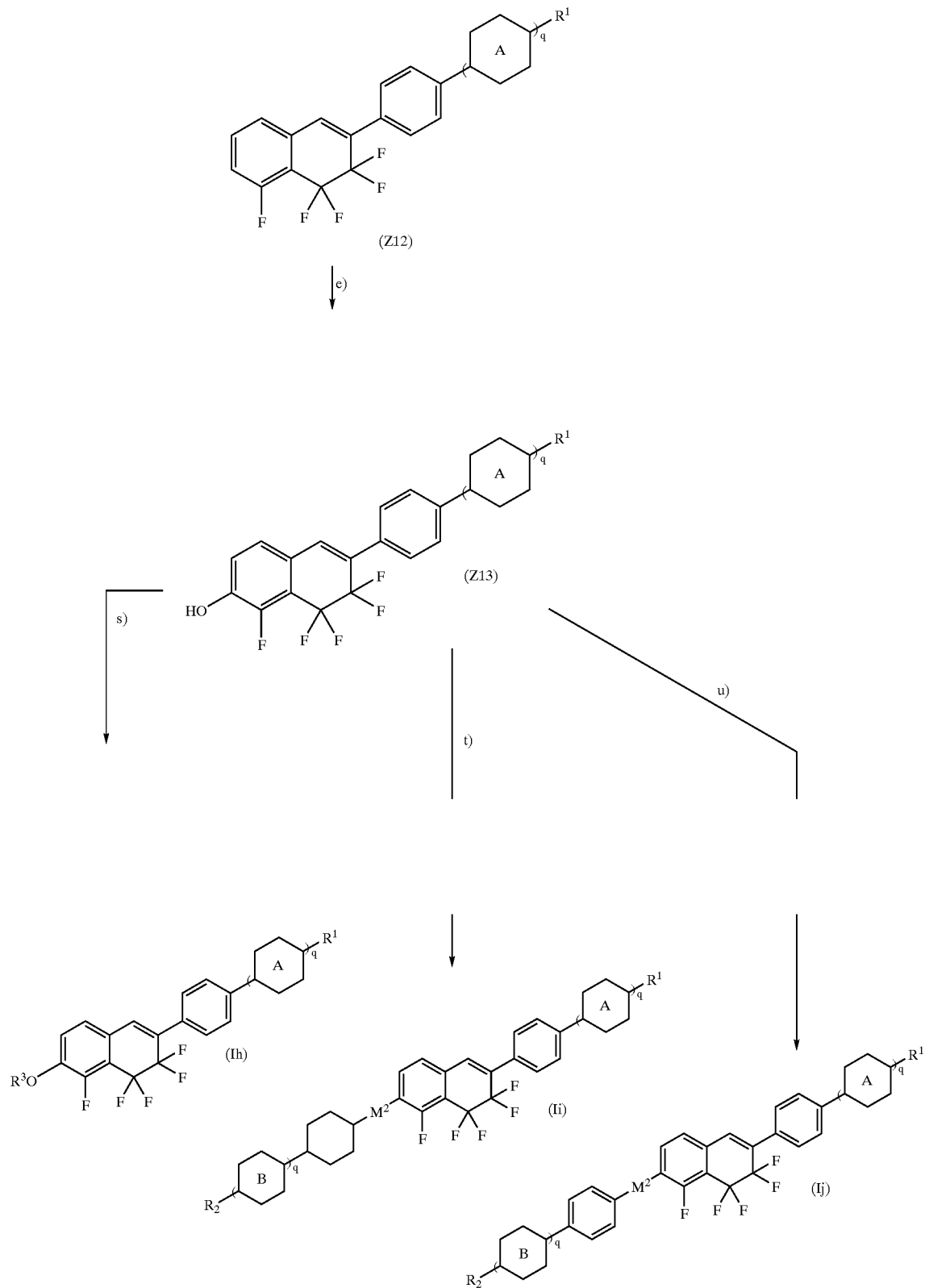

Scheme 4
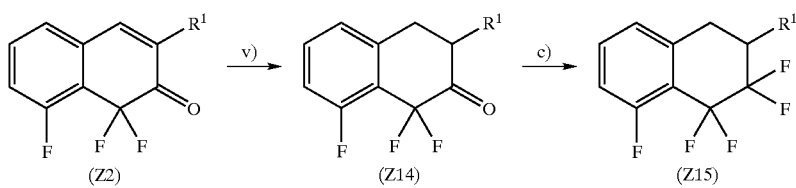
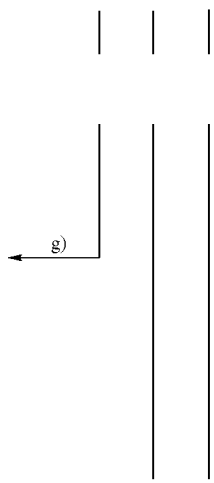
(Ik)
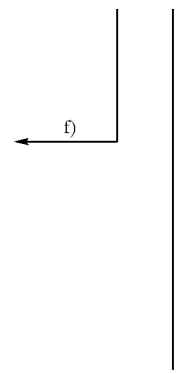
(Im)
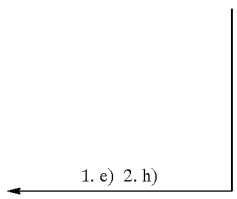
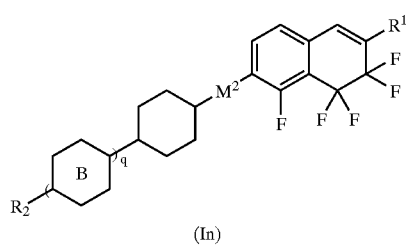
(In)

Scheme 5

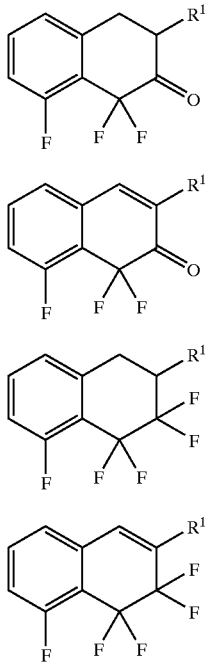

(Z14)

(Z2)

(Z15)

(Z3)

a) $C_2H_4$ ($R^1=C_2H_5$), $AlCl_3$, $CH_2Cl_2$, irradiation analogously to Kakiuchi, *J. Org Chem.* 58, 2797 (1993)
b) F-TEDA-$BF_4$, $CH_3CN$ analogously to EP-A 0 952135
c) DAST, $CH_2Cl_2$ analogously to EP-A 0 952135
d) 1. ortho-ithiation analogously to *J. Chem. Soc. Perkin Trans I* 1995, 2729 2. $R^2$—X analogously to *Recl. Trav. Chim. Pays-Bas* 113, 529 (1994)
e) 1.ortho-lithiation 2. $B(OMe)_3$ 3. $H^+$ 4. $H_2O_2/Et_2O$ analogously to *J. Chem. Soc. Perkin Trans II* 1989, 2041
f) 1. ortho-lithiation 2. $B(OMe)_3$ 3. $H^+$ 4. $R^2$—$(B)_q$—$C_6H_4$—Br, Pd catalyst, $Na_2CO_3$, toluene/ethanol/$H_2O$ analogously to *J. Chem. Soc. Perkin Trans II* 1989, 2041
g) 1. ortho-lithiation 2. $R^2$—$(B)_q$-cyclohexanone 3. $H^+$ 4. $H_2$, Pd/C (5%), toluene analogously to WO 96/00710
h) e.g. $R^2$—$(B)_q$—$C_6H_{10}CH_2Br$, $K_2CO_3$, 2-butanone for $M^2$=—$CH_2O$— or $R^2$—$(B)_q$—$C_6H_4CO_2H$, DCC, $CH_2Cl_2$ for $M^2$=—C(=O)O—
i) $HNO_3$/HOAc: Gillespie, *J. Org. Chem.* 39, 3239 (1974)
j) HBr/HOAc: Gillespie, *J. Org. Chem.* 39, 3239 (1974)
k) Trifluoromethanesulfonic anhydride/pyridine analogously to *Liq. Cryst.* 18, 1 (1995)
l) $R^2$—$(A)_q$—$C_6H_4$—Br, Pd catalyst, $Na_2CO_3$, toluene/ethanol/$H_2O$ analogously to *J. Chem. Soc. Perkin Trans II* 1989, 2041
m) Sn, HCl analogously to Dewar, *J. Am. Chem. Soc.* 84, 3782 (1962)
n) 1. $NaNO_2$ 2. $HBF_4$ 3. Thermolysis analogously to Corral, *Heterocycles* 23, 1431 (1985)
o) F-TEDA-$BF_4$, $CH_3CN$ analogously to EP-A 0 952135
p) DAST, $CH_2Cl_2$ analogously to EP-A 0 952135
q) 1. ortho-lithiation 2. $B(OMe)_3$ 3. $H^+$ 4. $R^2$—$(B)_q$—$C_6H_4$—Br, Pd catalyst, $Na_2CO_3$, toluene/ethanol/$H_2O$ analogously to *J. Chem. Soc. Perkin Trans II* 1989, 2041
r) 1. ortho-lithiation analogously to *J. Chem. Soc. Perkin Trans I* 1995, 2729 2. $R^2$—X analogously to *Recl. Trav. Chim. Pays-Bas* 113, 529 (1994)
s) $R^3$—X, $K_2CO_3$, 2-propanone (X=Br, I)
t) e.g. $R^2$—$(B)_q$—$C_6H_{10}CH_2Br$, $K_2CO_3$, 2-butanone for $M^2$=—$CH_2O$—
u) e.g. $R^2$—$(B)_q$—$C_6H_4CO_2H$, DCC, $CH_2Cl_2$ for $M^2$=—C(=O)O—
v) $H_2$, Pd/C analogously to *Tetrahedron Letters* 40, 3827 (1999)
w) DDQ, toluene analogously to EP-B 946474

The starting materials are known from the literature:
(E1): [13916-98-8]: Adcock, J. Am. Chem. Soc. 89, 386 (1967)
(E2): [10103-06-7], (Z6): [7311-22-0]: Bell, J. Chem. Soc. C, 904 (1966)

The further conversion of the functional derivatives of the compounds (I) in Schemes 1 to 5 into the final compounds is carried out by methods familiar to the person skilled in the art.

In the liquid-crystal media according to the present application, compounds of formula I and the formulae given in Tables A and B, particularly those of formula I and those given in Table A, are preferably employed in a concentration of up to about 25% per individual substance. Compounds of the formulae given in Table B are preferably employed in a concentration of up to about 20%, preferably up to 16%, per individual substance. Compounds of the formula I, preferably of the formulae I-1 to I-3, are preferably employed in concentrations of up to about 15%, preferably up to 10%, per individual substance.

In the present application, "≦" means less than or equal to, preferably less than, and "≧" means greater than or equal to, preferably greater than.

In the present application,

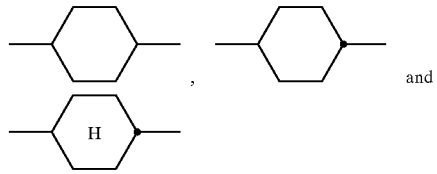

and denote trans-1,4-cyclohexylene.

In the present application, the term dielectrically positive compounds denotes compounds having a Δε of >1.5, the term dielectrically neutral compounds denotes compounds where −1.5≦Δε≦1.5, and the term dielectrically negative compounds denotes compounds where Δε<−1.5. The dielectric anisotropy of the compounds is determined here by dissolving 10% of the compounds in a liquid-crystalline host and measuring the capacitance of this mixture at 1 kHz in at least one test cell in each case with a layer thickness of 20 μm and a homeotropic and homogeneous surface alignment. The measurement voltage is typically from 0.5 V to 1.0 V, but is always less than the capacitive threshold of the particular liquid-crystal mixture.

The host mixture used is generally ZLI-4792, but ZLI-2857, also from Merck KGaA, Germany, is used for the determination of the dielectric anisotropy of dielectrically negative compounds. The values for the respective compounds to be investigated are obtained from the change in the dielectric constants of the host mixture after addition of the compound to be investigated and extrapolation to 100% of the compound employed.

The term threshold voltage usually relates to the optical threshold for 10% relative contrast ($V_{10}$), unless explicitly stated otherwise.

In the present application, however, the term threshold voltage in relation to liquid-crystal mixtures of negative dielectric anisotropy is used for the capacitive threshold voltage ($V_0$), also known as the Freedericksz threshold, unless explicitly stated otherwise.

All concentrations in this application, unless explicitly stated otherwise, are given in percent by weight and relate to the corresponding mixture or mixture component. All physical properties are and have been determined as described in "Merck Liquid Crystals, Physical Properties of Liquid Crystals", Status November 1997, Merck KGaA, Germany, and apply to a temperature of 20° C., unless explicitly stated otherwise. Δn is determined at 589 nm and Δε at 1 kHz.

In the case of the liquid-crystal media of negative dielectric anisotropy, the threshold voltage was determined as the capacitive threshold $V_0$ (also known as the Freedericksz threshold) in test cells manufactured at Merck KGaA, Germany, with a liquid crystal aligned homeotropically by the alignment layer SE 1211 from Nissan Chemicals.

The liquid-crystal media according to the invention may, if necessary, also comprise further additives and chiral dopants in the usual amounts. The amount of these additives employed is in total from 0% to 10%, based on the amount of the mixture as a whole, preferably from 0.1% to 6%. The concentrations of the individual compounds employed are preferably from 0.1% to 3%. The concentration of these and similar additives is not taken into account when indicating the concentrations and the concentration ranges of the liquid-crystal compounds in the liquid-crystal media.

The compositions consist of a plurality of compounds, preferably from 3 to 30, particularly preferably from 6 to 20 and very particularly preferably from 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituent, the completeness of the dissolution operation can be observed particularly easily. However, it is also possible to prepare the liquid-crystal mixtures in other conventional ways, for example using premixes or from a so-called "multibottle system".

By means of suitable additives, the liquid-crystal phases according to the invention can be modified in such a way that they can be employed in any type of ECB, VAN, IPS, GH or ASM-PA LCD display disclosed hitherto.

The entire disclosure of all applications, patents and publications, cited above and below, and of corresponding German Application No. 10225427.3, filed Jun. 7, 2002, is hereby incorporated by reference.

The following examples serve to illustrate the invention without restricting it. In the examples, the melting point T (C,N), the smectic (S) to nematic (N) phase transition T (S,N) and the clearing point T (N,I) of a liquid-crystal substance are indicated in degrees Celsius.

Unless stated otherwise, all percentages above and below are percent by weight, and the physical properties are the values at 20° C., unless explicitly indicated otherwise.

All values indicated for temperatures in this application are ° C. and all temperature differences correspond to differential degrees, unless explicitly stated otherwise. In the present application and in the following examples, the structures of the liquid-crystal compounds are indicated by means of acronyms, with the transformation into chemical formulae taking place in accordance with the following tables A and B. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In individual cases, the acronym for the parent structure is followed, separated by a dash, by a code for the substituents $R^1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| nmFF | $C_nH_{2n+1}$ | $C_mH_{2m+1}$ | H | F | F |
| nOmFF | $C_nH_{2n+1}$ | $OC_mH_{2m+1}$ | H | F | F |
| n | $C_nH_{2n+1}$ | CN | H | H | H |
| nN.F | $C_nH_{2n+1}$ | CN | F | H | H |
| nN.F.F | $C_nH_{2n+1}$ | CN | F | F | H |
| nF | $C_nH_{2n+1}$ | F | H | H | H |
| nF.F | $C_nH_{2n+1}$ | F | F | H | H |
| nF.F.F | $C_nH_{2n+1}$ | F | F | F | H |
| nOF | $OC_nH_{2n+1}$ | F | H | H | H |
| nCl | $C_nH_{2n+1}$ | Cl | H | H | H |
| nCl.F | $C_nH_{2n+1}$ | Cl | F | H | H |
| nCl.F.F | $C_nH_{2n+1}$ | Cl | F | F | H |
| $nCF_3$ | $C_nH_{2n+1}$ | $CF_3$ | H | H | H |
| $nCF_3$.F | $C_nH_{2n+1}$ | $CF_3$ | F | H | H |
| $nCF_3$.F.F | $C_nH_{2n+1}$ | $CF_3$ | F | F | H |
| $nOCF_3$ | $C_nH_{2n+1}$ | $OCF_3$ | H | H | H |
| $nOCF_3$.F | $C_nH_{2n+1}$ | $OCF_3$ | F | H | H |
| $nOCF_3$.F.F | $C_nH_{2n+1}$ | $OCF_3$ | F | F | H |
| $nOCF_2$ | $C_nH_{2n+1}$ | $OCHF_2$ | H | H | H |
| $nOCF_2$.F | $C_nH_{2n+1}$ | $OCHF_2$ | F | H | H |
| $nOCF_2$.F.F | $C_nH_{2n+1}$ | $OCHF_2$ | F | F | H |
| nS | $C_nH_{2n+1}$ | NCS | H | H | H |
| nS.F | $C_nH_{2n+1}$ | NCS | F | H | H |
| nS.F.F | $C_nH_{2n+1}$ | NCS | F | F | H |
| rVsN | $C_rH_{2r+1}$—CH=CH—$C_sH_{2s}$— | CN | H | H | H |
| rEsN | $C_rH_{2r+1}$—O—$C_sH_{2s}$— | CN | H | H | H |

TABLE A

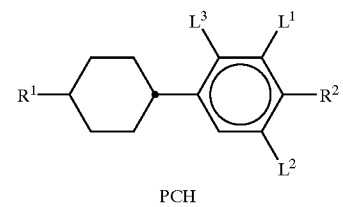

PCH

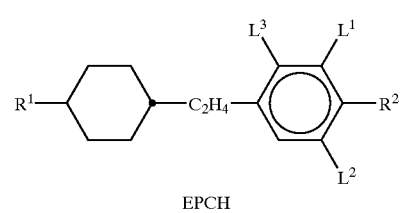

EPCH

TABLE A-continued
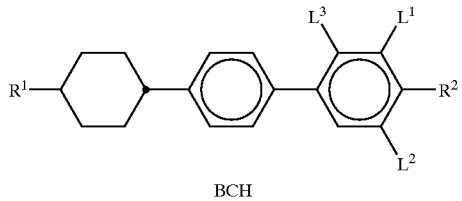
BCH
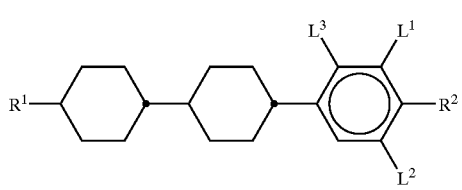
CCP
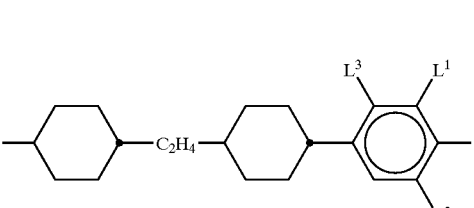
CECP
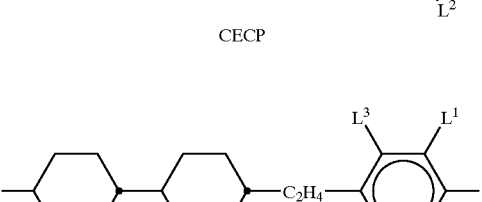
ECCP
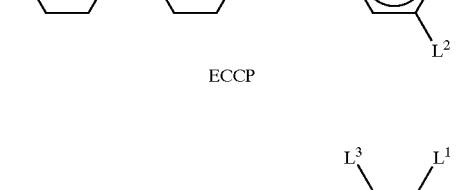
BECH
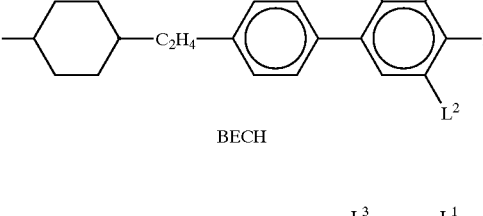
EBCH
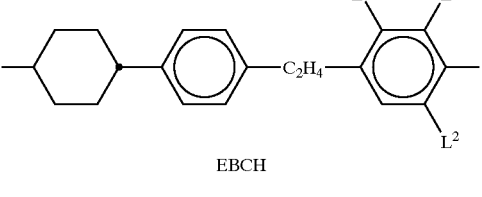
PTP
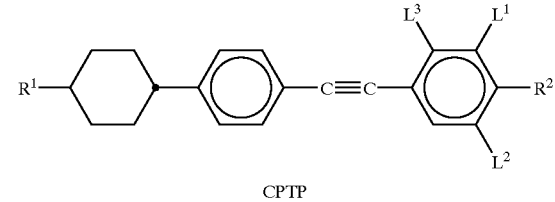
CPTP
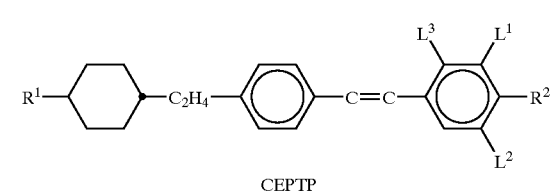
CEPTP
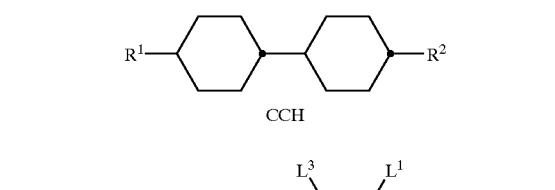
CCH
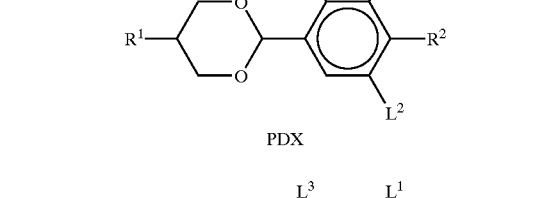
PDX
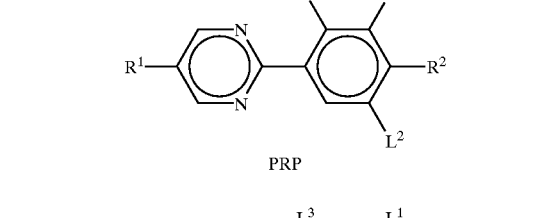
PRP
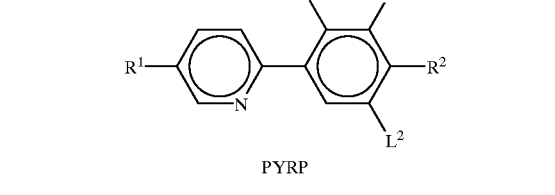
PYRP
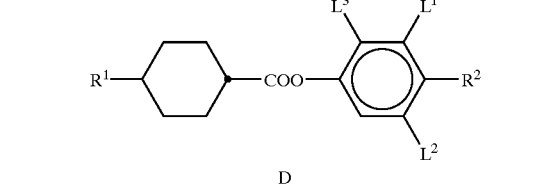
D
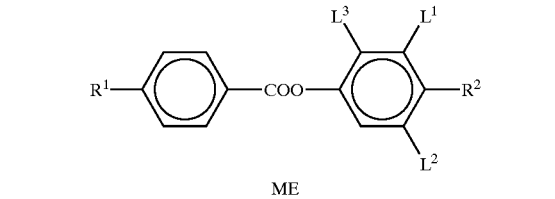
ME TABLE A-continued
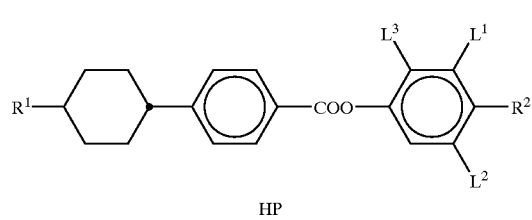
HP
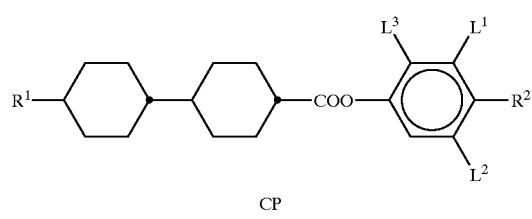
CP
TABLE A-continued
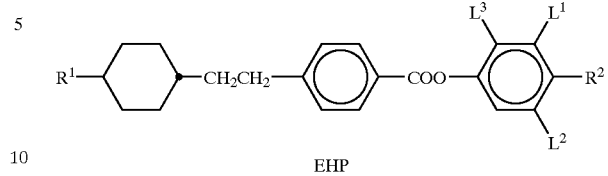
EHP
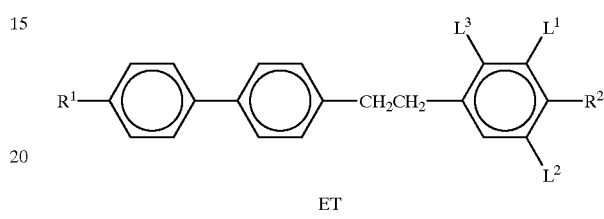
ET
TABLE B
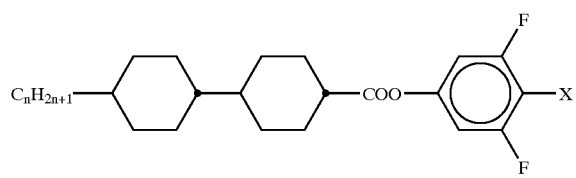
CCZU-n-X
(X = F, Cl or OCF$_3$)
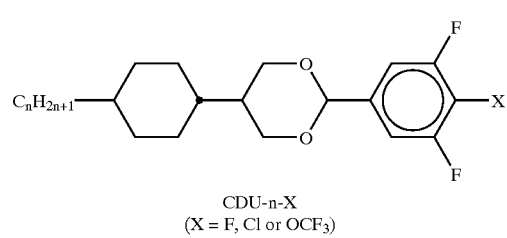
CDU-n-X
(X = F, Cl or OCF$_3$)
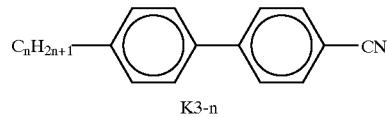
K3-n
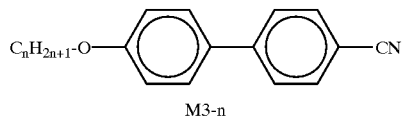
M3-n
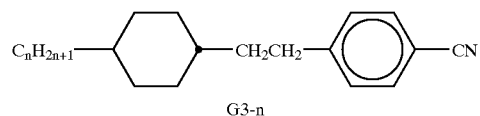
G3-n TABLE B-continued
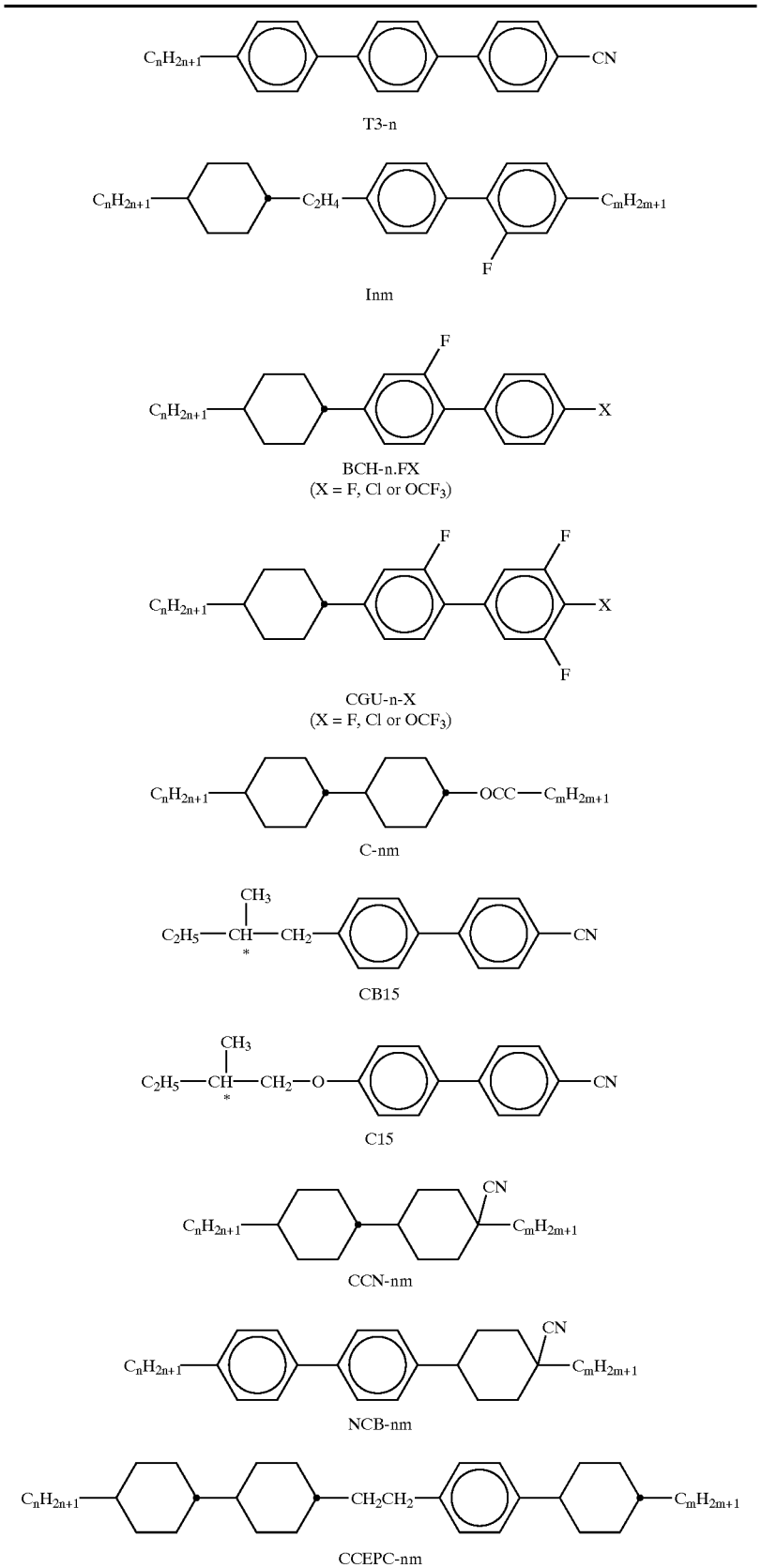

TABLE B-continued
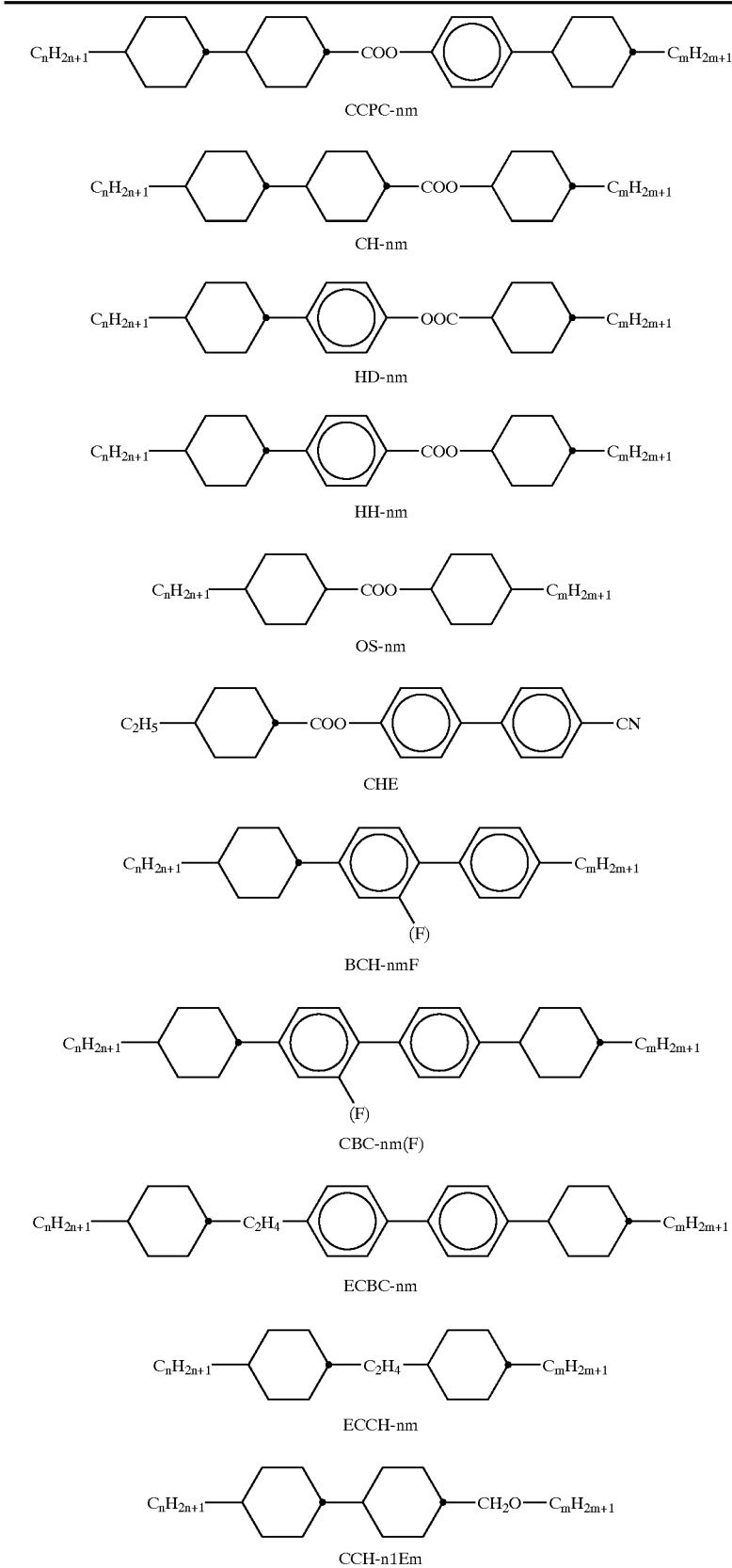

TABLE B-continued
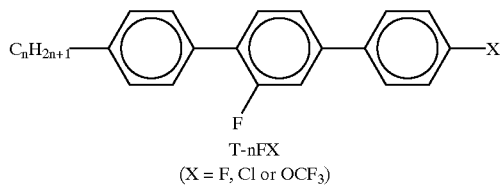
T-nFX
(X = F, Cl or OCF$_3$)
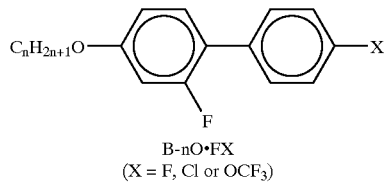
B-nO•FX
(X = F, Cl or OCF$_3$)
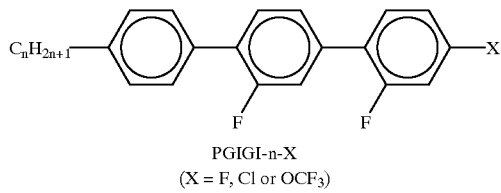
PGIGI-n-X
(X = F, Cl or OCF$_3$)
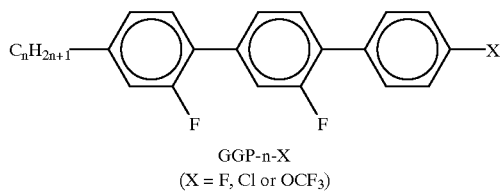
GGP-n-X
(X = F, Cl or OCF$_3$)
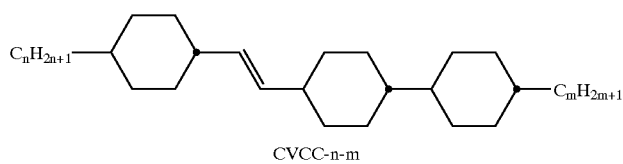
CVCC-n-m
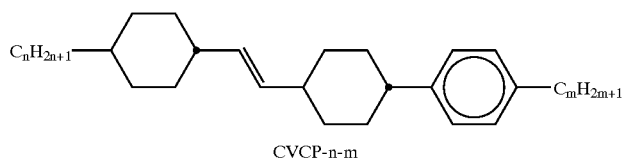
CVCP-n-m
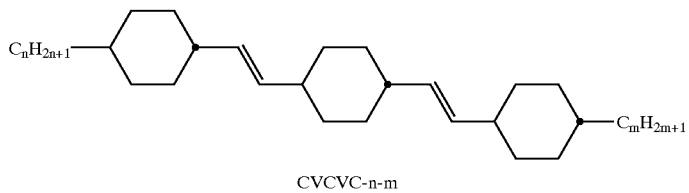
CVCVC-n-m
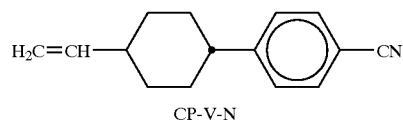
CP-V-N TABLE B-continued
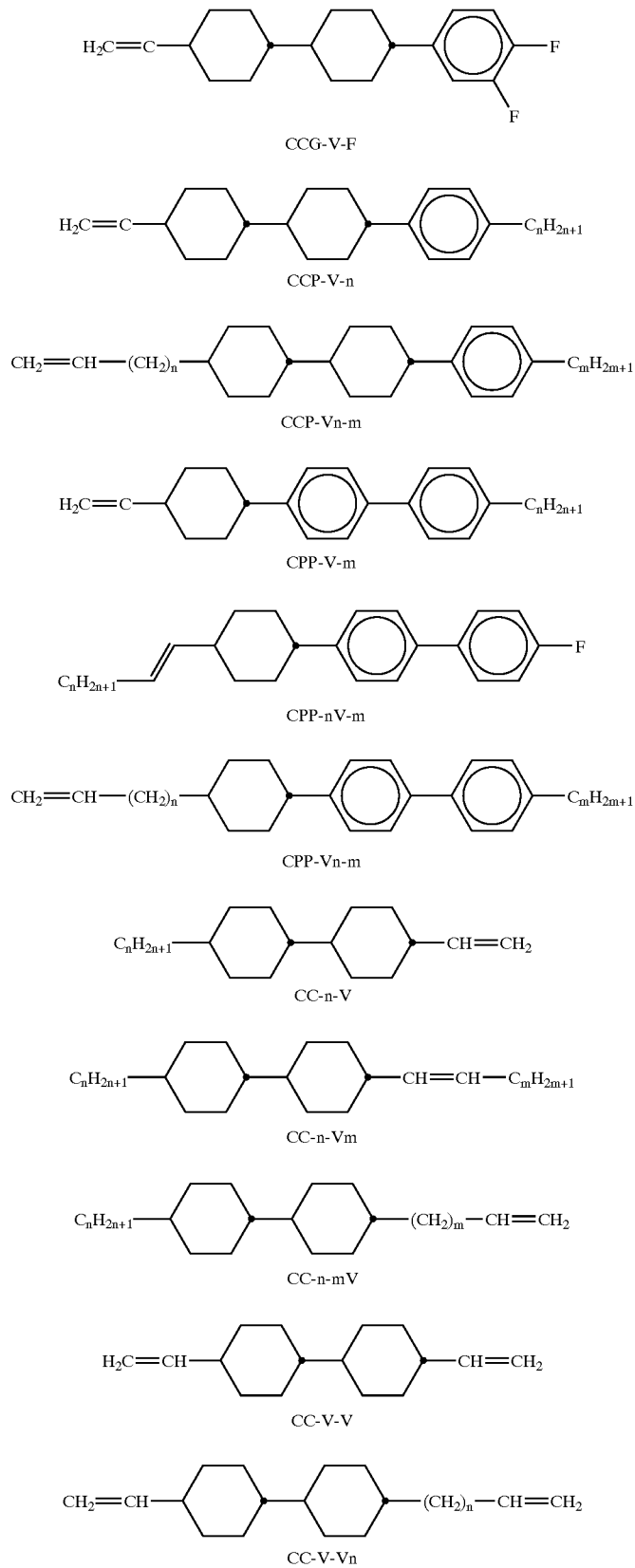

TABLE B-continued
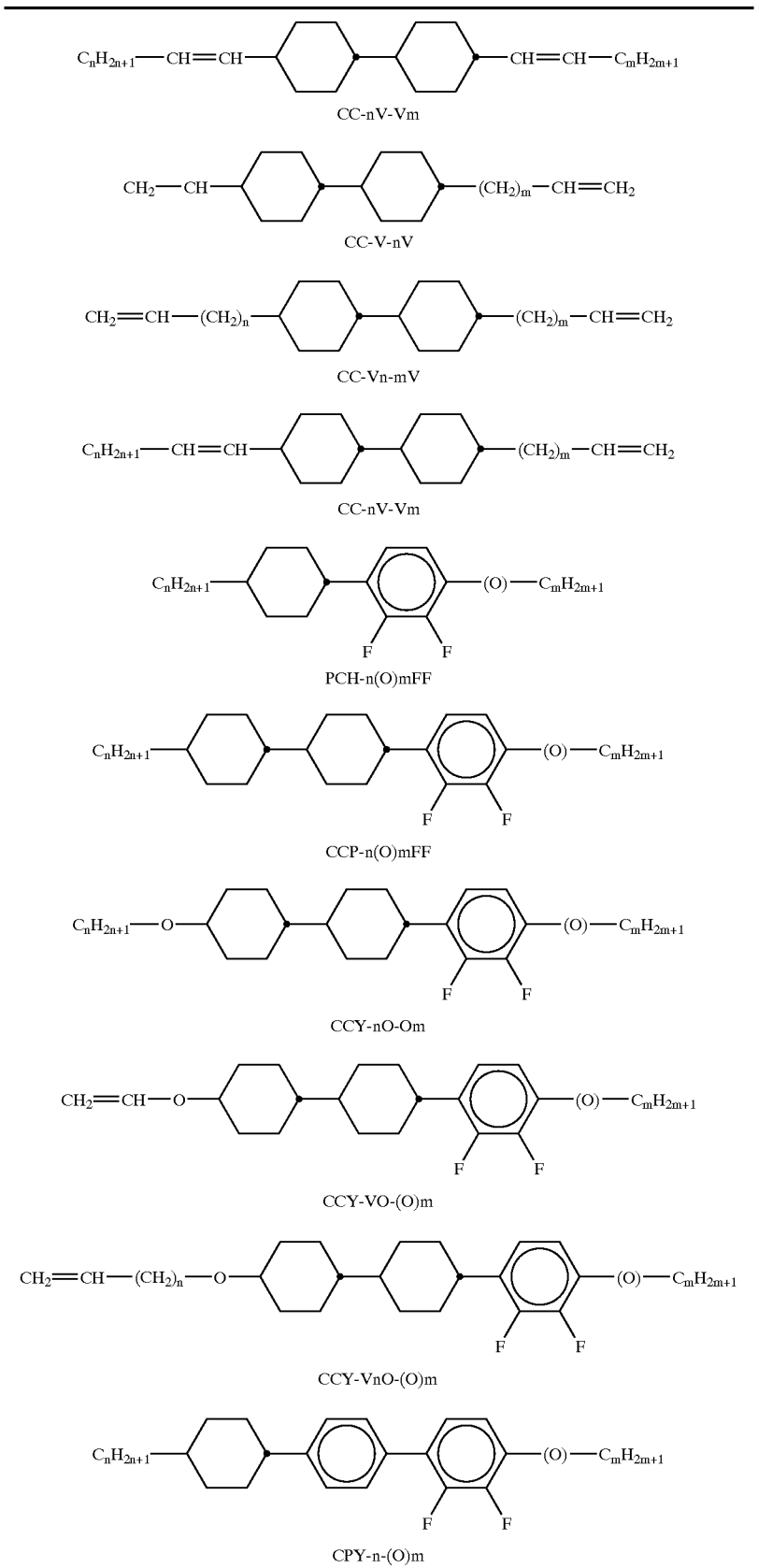

TABLE B-continued
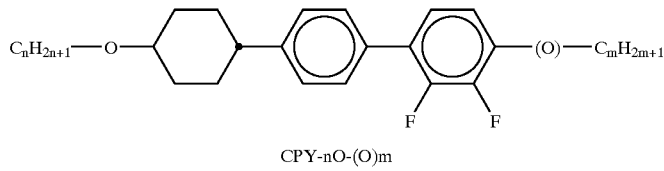
CPY-nO-(O)m
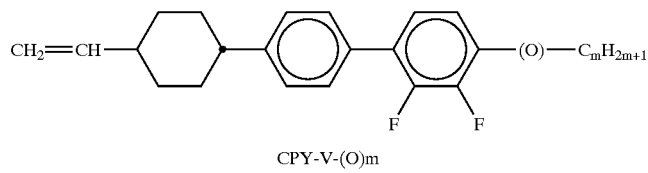
CPY-V-(O)m
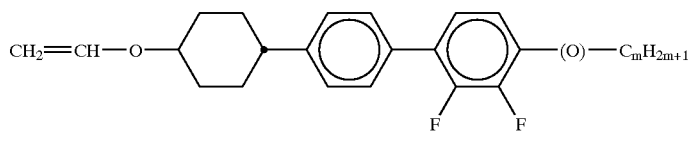
CPY-VO-(O)m
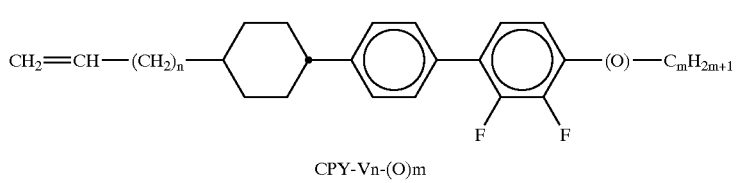
CPY-Vn-(O)m
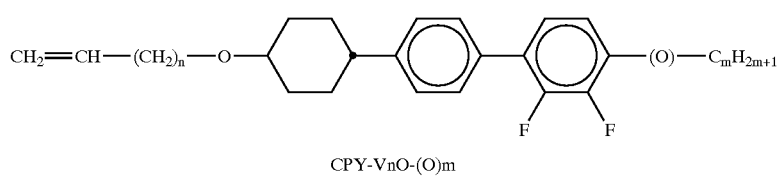
CPY-VnO-(O)m
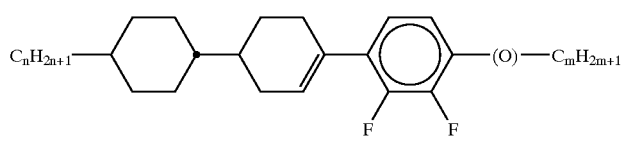
CLY-n-(O)m
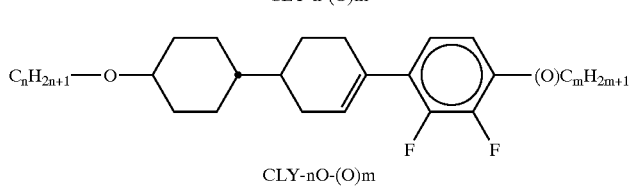
CLY-nO-(O)m
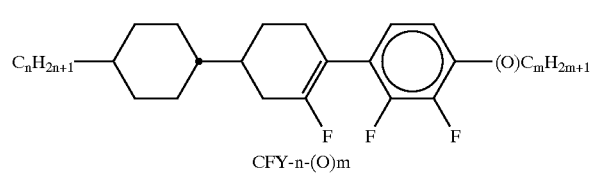
CFY-n-(O)m
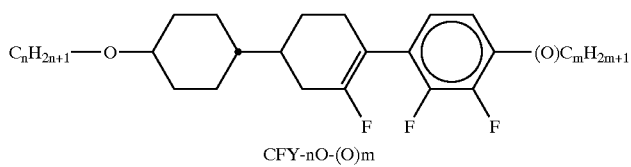
CFY-nO-(O)m TABLE B-continued
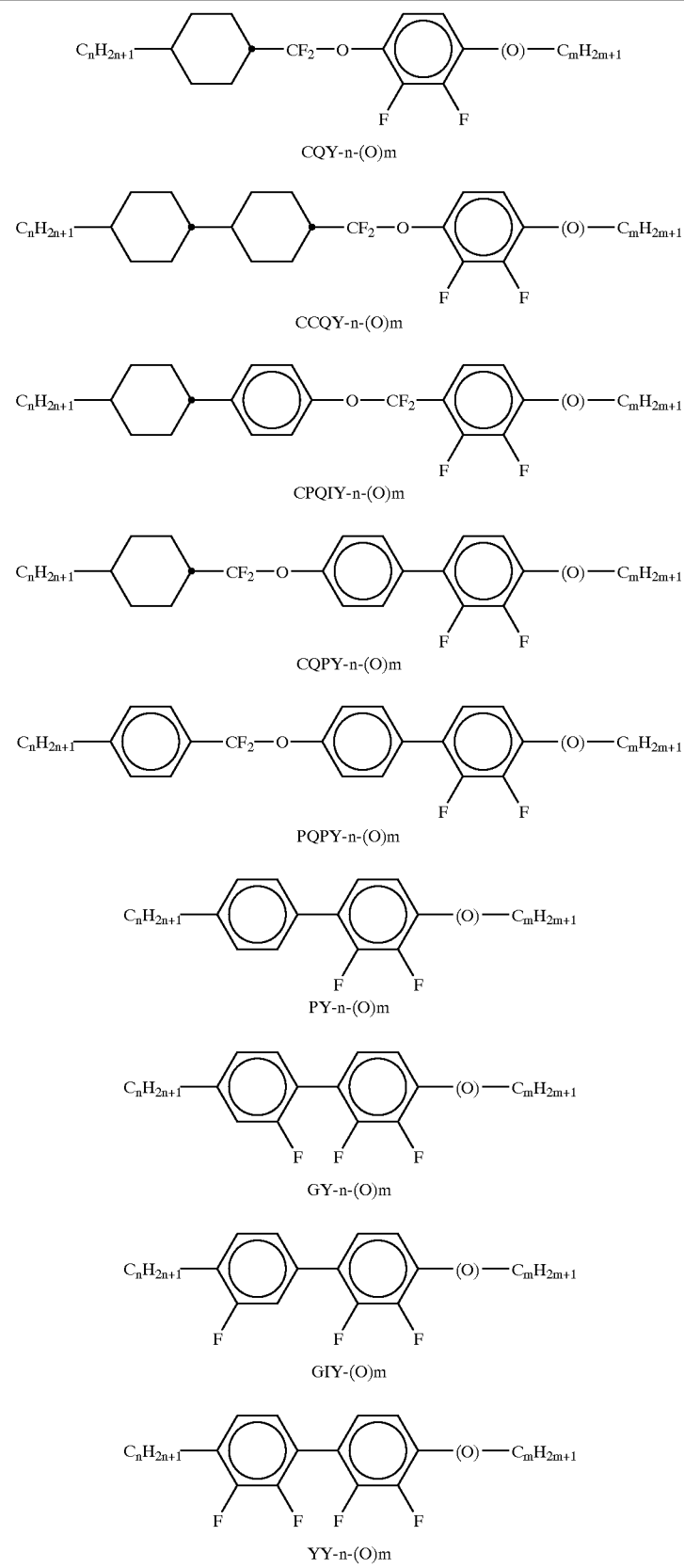

TABLE B-continued
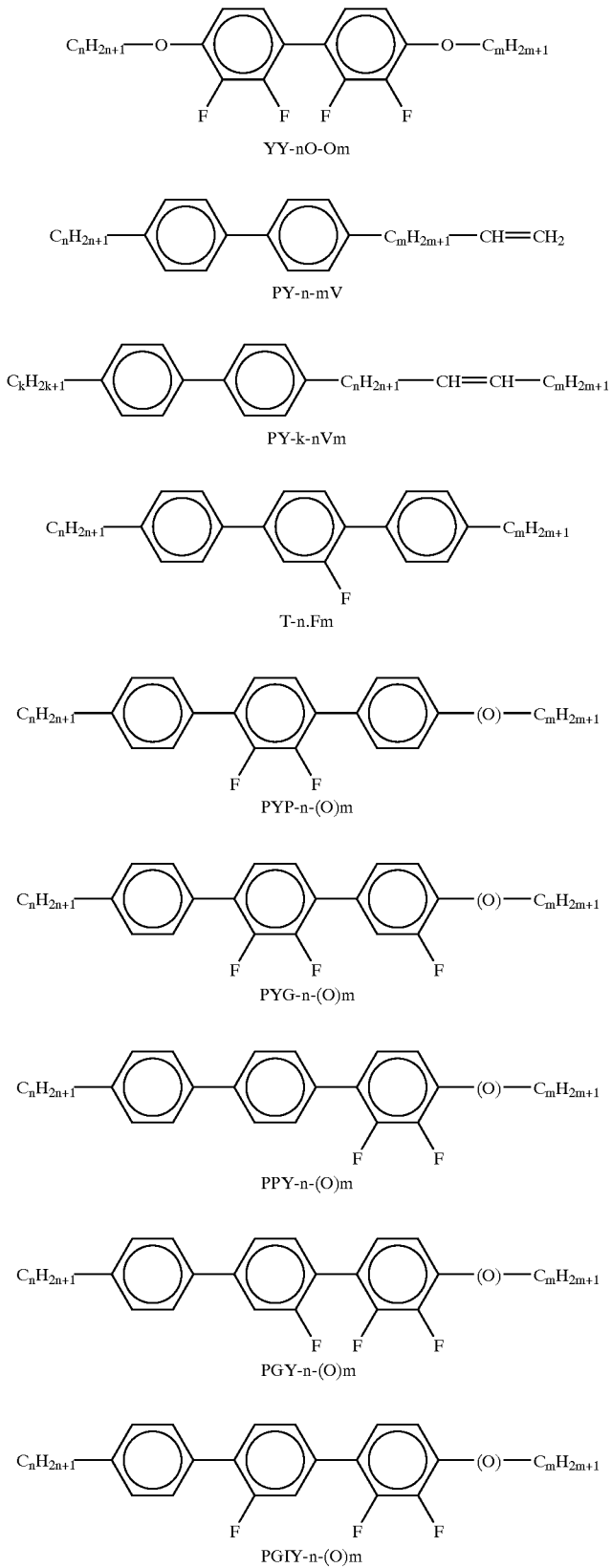

TABLE B-continued
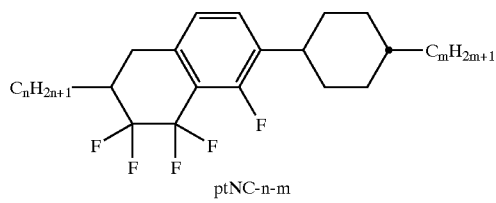
ptNC-n-m
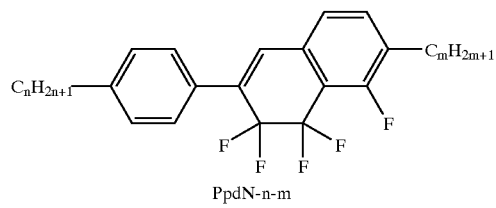
PpdN-n-m
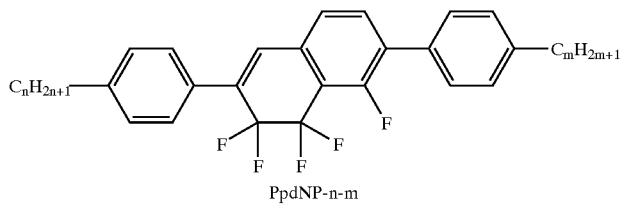
PpdNP-n-m
TABLE C
Table C indicates dopants which are usually employed in the mixtures according to the invention.
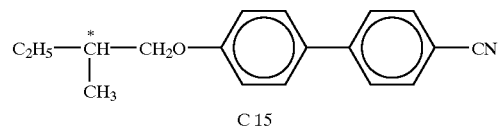
C 15
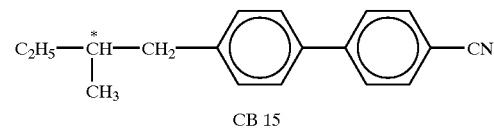
CB 15
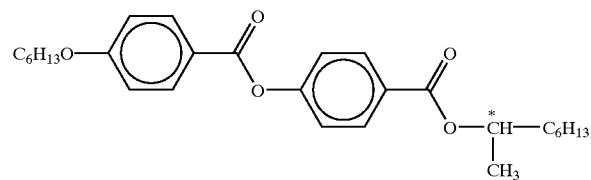
R/S-811
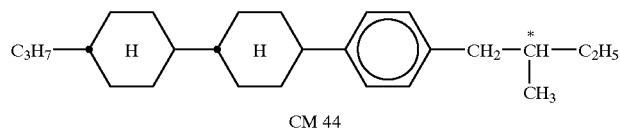
CM 44

TABLE C-continued
Table C indicates dopants which are usually employed in the mixtures according to the invention.
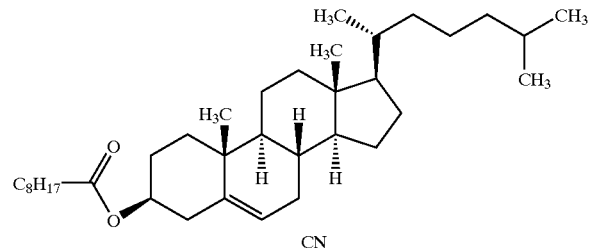
CN
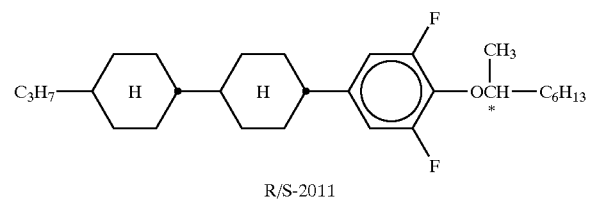
R/S-2011
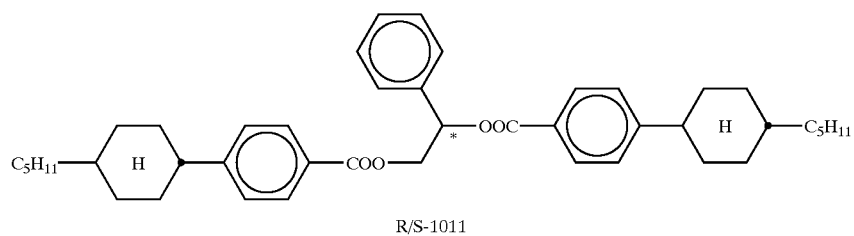
R/S-1011
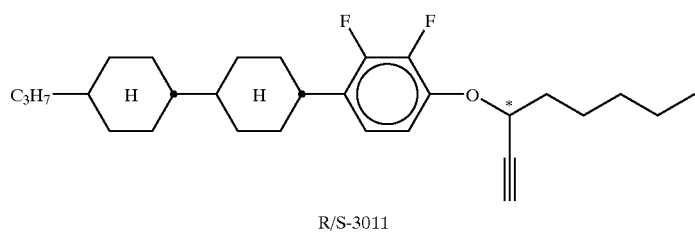
R/S-3011
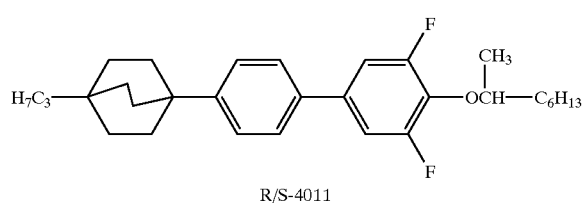
R/S-4011

TABLE D
Stabilisers which can, for example, be added to the mixtures according to the invention are indicated below.
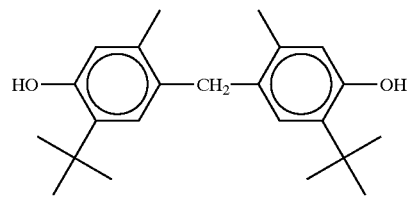
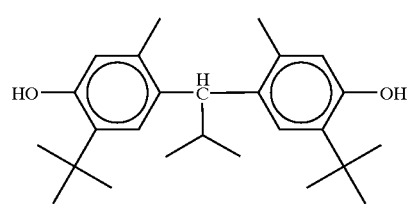
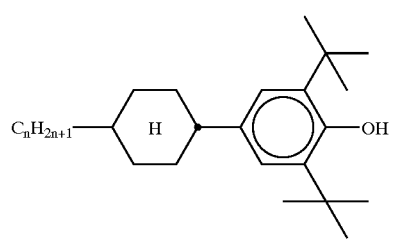
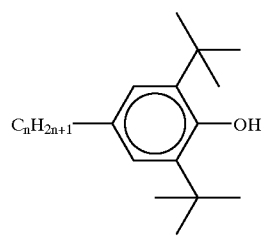
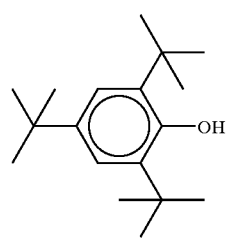
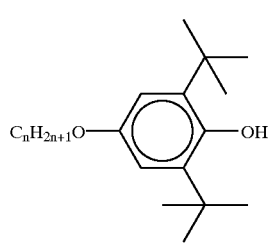
TABLE D-continued
Stabilisers which can, for example, be added to the mixtures according to the invention are indicated below.
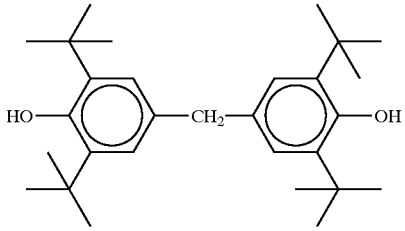
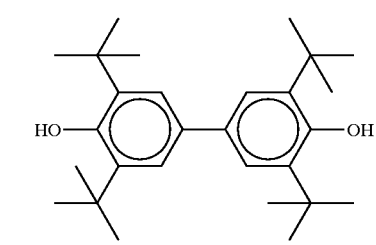
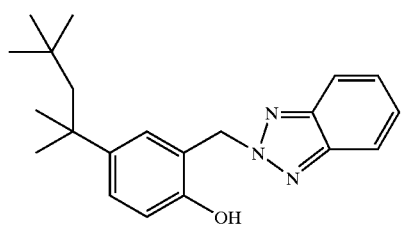
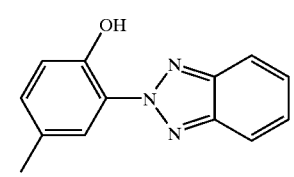
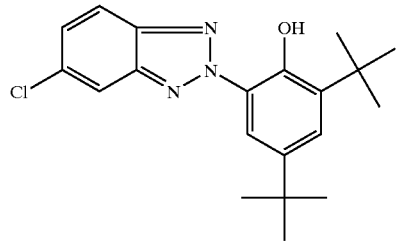
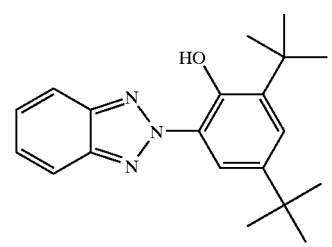

TABLE D-continued

Stabilisers which can, for example, be added to the mixtures according to the invention are indicated below.

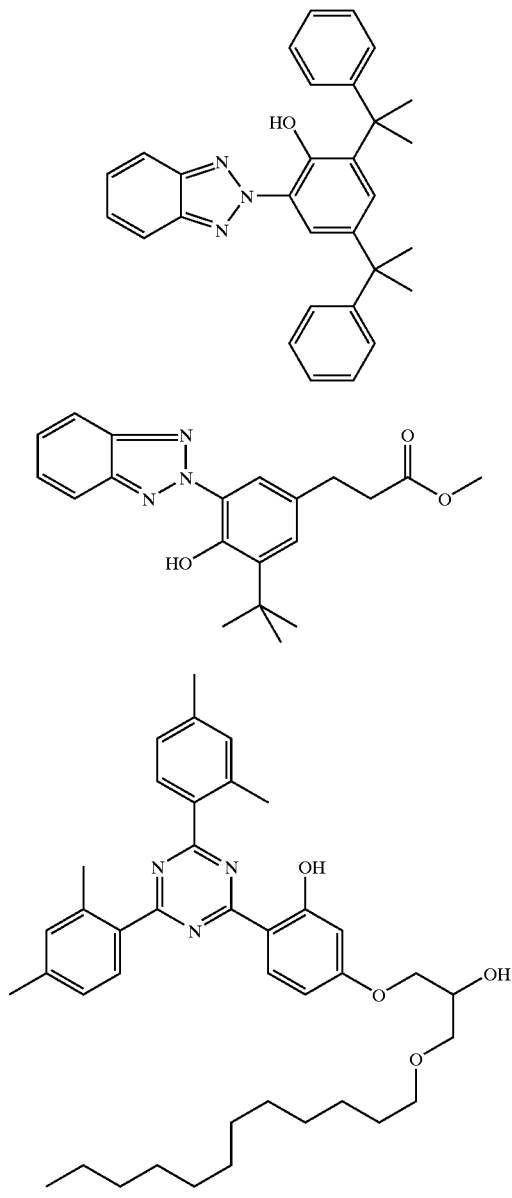

The liquid-crystal media according to the invention preferably comprise five or more, particularly preferably six or more and very particularly preferably seven or more compounds selected from the formulae of Tables A and B.

The liquid-crystal media according to the invention preferably comprise two or more, particularly preferably three or more and very particularly preferably four or more compounds selected from the formulae of Table A.

The liquid-crystal media according to the invention preferably comprise three or more, particularly preferably four or more and very particularly preferably five or more compounds selected from the formulae of Table B.

These compounds are preferably compounds of various formulae from these tables.

EXAMPLES

The following examples are intended to explain the invention without limiting it. Above and below, percentages are percent by weight. All temperatures are indicated in degrees Celsius. $\Delta n$ denotes optical anisotropy (589 nm, 20° C.), $\Delta\epsilon$ denotes the dielectric anisotropy (1 kHz, 20° C.), H.R. denotes the voltage holding ratio (at 100° C., after 5 minutes in the oven, 1 V), and $V_0$ denotes the threshold voltage, determined at 20° C.

Example 1

1,1,2,2,8-Pentafluoro-7-(4-propylphenyl)-1,2-dihydronaphthalene

[(Ib1) where $R^1$=H, $R^2$=$C_3H_7$]

A solution of 4.8 g of 1,1,2,2,8-pentafluoro-1,2-dihydronaphthalene [(Z3) where $R^1$=H] in 75 ml of tetrahydrofuran was mixed with 11 ml of sec-butyllithium (2M in pentane) at a temperature below −75° C. After 3 g of trimethyl borate had been added, the mixture was stirred at the same temperature for 3 hours and subsequently brought to room temperature overnight. After hydrolysis using 10% hydrochloric acid, 150 ml of tert-butyl methyl ether were added, and the organic phase was separated off, washed with water and sodium chloride solution and dried. The 1,1,2,2,8-pentafluoro-1,2-dihydronaphthalene-7-boronic acid obtained was reacted with the equimolar amount of 4-propylbromobenzene, 2 mol-equivalents of sodium carbonate and 1 mol % of tetrakis(triphenylphosphine)palladium(0) in 50 ml of an ethanol/toluene/water 1:2:1 (vol.) mixture by refluxing for one day. After conventional work-up, the organic fraction was subjected to chromatographic purification (silica gel, toluene/heptane 2:1), the product-containing fractions were combined, the solvent mixture was distilled off under reduced pressure, and the residue was recrystallised from acetonitrile, giving 1.6 g of 1,1,2,2,8-pentafluoro-7-(4-propylphenyl)-1,2-dihydronaphthalene.

Example 2

3-Ethyl-1,1,2,2,8-pentafluoro-7-(4-propylphenyl)-1,2-dihydronaphthalene

[(Ib1) Where $R^1$=$C_2H_5$, $R^2$=$C_3H_7$]

was obtained analogously to Example 1.

Example 3

7-Ethoxy-3-(4-ethylphenyl)-1,1,2,2,8-pentafluoro-1,2-dihydronaphthalene

[(Ih1) where $R^1$=$C_2H_5$, $R^3$=$C_2H_5$]

was obtained by reaction of 10.9 g of (Z7) with 5.3 g of 4-ethylphenylboronic acid, 2 mol-equivalents of potassium carbonate and 1 mol % of tetrakis(triphenylphosphine)palladium(0) in 70 ml of ethanol/toluene/water 1:2:1 by refluxing for a number of hours, followed by standard work-up as described in Example 1. The compound obtained [(Z8) where q=0 and $R^1$=$C_2H_5$] was reduced to (Z9) by means of tin granules in a hydrochloric acid/tetrahydrofuran mixture, and (Z9) was, without further purification, subjected to a Baltz-Schiemann reaction to give 3-(4-ethylphenyl)-8-fluoro-2-methoxynaphthalene [(Z10) where q=0 and $R^1$=$C_2H_5$]. 2 mol-equivalents of F-TEDA-$BF_4$ were added to a solution of 3 g of this compound in 100 ml of acetonitrile at room temperature; when the reaction was complete, the product was purified by chromatography (silica gel, dichloromethane). 2 mol-equivalents of DAST in 50 ml of dichloromethane were added to the crude 3-(4-ethylphenyl)-1,1,8-trifluoro-1H-naphthalen-2-one [(Z11) where q=0 and $R^1$=$C_2H_5$], and the mixture was refluxed until the reaction was complete. After careful hydrolysis, the product was purified by chromatography (silica gel, dichloromethane), giving 0.4 g of 3-(4-ethylphenyl)-1,1,2,2,8-pentafluoro-1,2-dihydronaphthalene [(Z12) where q=0 and $R^1$=$C_2H_5$]. This was converted under the conditions of the ortho-lithiation from Example 1 into the corresponding boronic acid, which, after isolation from the reaction mixture, was converted in crude form by means of hydrogen peroxide in diethyl ether into 3-(4-ethylphenyl)-7-hydroxy-1,1,2,2,8-pentafluoro-1,2-dihydronaphthalene [(Z13) where q=0 and $R^1$=$C_2H_5$]. The latter compound was converted by heating for several hours with 1.5 mol-equivalents of ethyl iodide in the presence of 3 mol-equivalents of potassium carbonate in acetone, into 7-ethoxy-3-(4-ethylphenyl)-1,1,2,2,8-pentafluoro-1,2-dihydronaphthalene, which was purified by chromatography (silica gel, toluene) and by recrystallisation (acetonitrile).

Examples 4 to 23

The following are prepared analogously:

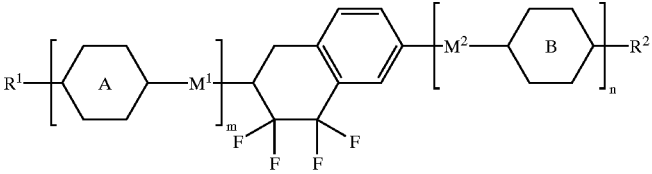

| No. | $R^1\!-\!\left[\!-\!\bigcirc\!A\!-\!M^1\!-\!\right]_m\!\!-\!*$ | $*\!-\!\left[\!-\!M^2\!-\!\bigcirc\!B\!-\!\right]_n\!\!-\!R^2$ | Properties |
|---|---|---|---|
| 4 | 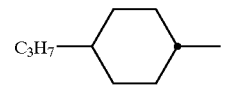 | —$C_3H_7$ | |
| 5 | 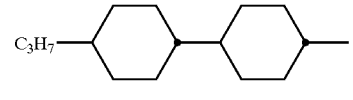 | —$C_3H_7$ | |
| 6 | $C_3H_7$— | 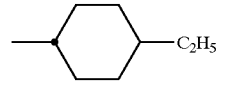 | $\Delta\epsilon$ = −7.8; $\Delta n$ = 0.074 |
| 7 | $C_3H_7$— | 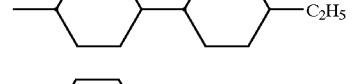 | $\Delta\epsilon$ = −6.0; $\Delta n$ = 0.074 |
| 8 | $C_3H_7$— | 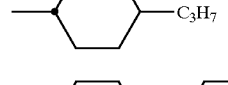 | |
| 9 | $C_3H_7$— | 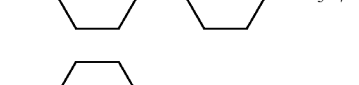 | |
| 10 | 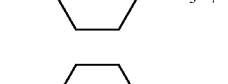 | 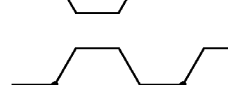 | |
| 11 | 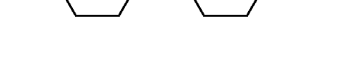 | | |
| 12 | | | |

-continued
| No. | $R^1-[A]_m-M^1-*$ | $*-M^2-[B]_n-R^2$ | Properties |
|---|---|---|---|
| 13 | 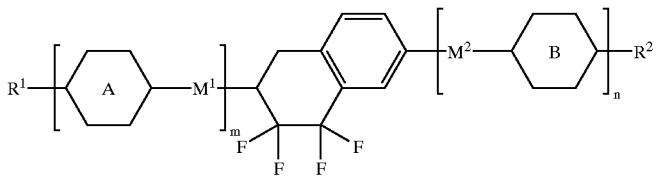 C₃H₇— | —CH₃ | Δε = −8.7<br>Δn = 0.107 |
| 14 | 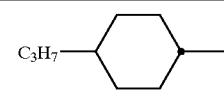 C₃H₇— | —O—C₂₅₇ | Δε = −11.4<br>Δn = 0.125 |
| 15 | 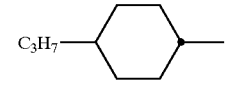 C₅H₁₁— | —CH₃ | Δε = −8.8<br>Δn = 0.165 |
| 16 | H₃C— | 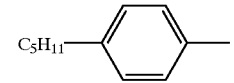 —C₅H₁₁ | Δε = −4.6<br>Δn = 0.106 |
| 17 | H₃C— | 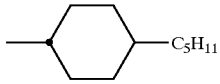 —C₃H₇ | Δε = −7.1<br>Δn = 0.173 |
| 18 | H₃C— | 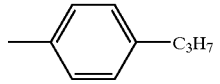 —O—CF₂— —C₃H₇ | Δε = −5.9<br>Δn = 0.094 |
| 19 | H₃C— | 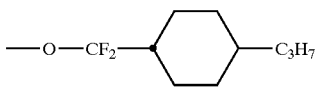 —C₃H₇ | Δε = −2.7<br>Δn = 0.192 |
| 20 | H₃C— | 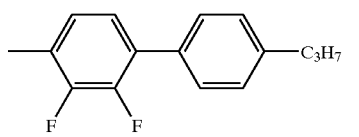 —C₃H₇ | |
| 21 | H₃C— | 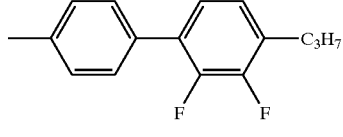 —C₃H₇ | |
| 22 | 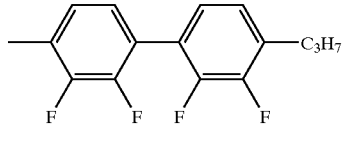 C₃H₇— | 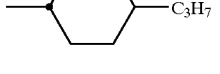 —C₃H₇ | Δε = −7.4<br>Δn = 0.100 |
| 23 | C₃H₇— | 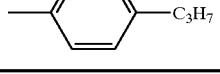 —C₃H₇ | Δε = −7.4<br>Δn = 0.209 |

Use Examples

Use Example 1

The liquid-crystal mixture of the compositions shown in the following table was prepared and investigated. The results of the physical properties are likewise shown in the following table.

| Compound/ abbreviation | Concentration/ % by weight | Physical properties | |
|---|---|---|---|
| PCH-304FF | 180 | T (N, I) = | 75.5° C. |
| PCH-502FF | 9.0 | Δn (20° C., 589 nm) = | 0.0818 |
| CCP-302FF | 8.0 | Δε (20° C., 1 kHz) = | −3.7 |
| CCP-303FF | 6.0 | $\gamma_1$ (20° C.) = | 115 mPa · s |
| CCP-402FF | 7.0 | $t_{store}$ (−30° C.) | > 1000 h |
| CPY-2-O2 | 9.0 | $V_0$ (20° C.) = | 2.10 V |
| CC-5-V | 20.0 | | |
| CC-3-V1 | 10.0 | | |
| CCH-35 | 8.0 | | |
| ptNC-3-3 | 5.0 | | |
| Σ | 100.0 | | |

The liquid-crystal medium is introduced into a VA display with TFT addressing. This display has a low addressing voltage and short response times.

Use Example 2

The liquid-crystal mixture of the compositions shown in the following table was prepared and investigated. The results of the physical properties are likewise shown in the following table.

| Compound/ abbreviation | Concentration/ % by weight | Physical properties | |
|---|---|---|---|
| PCH-304FF | 17.0 | T (N, I) = | 81.5° C. |
| PCH-502FF | 12.0 | Δn (20° C., 589 nm) = | 0.1284 |
| CPY-2-O2 | 12.0 | Δε (20° C., 1 kHz) = | −3.7 |
| CPY-3-O2 | 12.0 | $\gamma_1$ (20° C.) = | 155 mPa · s |
| BCH-32 | 10.0 | $t_{store}$ (20° C.) | > 1000 h |
| CC-5-V | 5.0 | $V_0$ (20° C.) = | 2.10 V |
| CC-3-V1 | 12.0 | | |
| CCP-V-1 | 6.0 | | |
| CCH-35 | 6.0 | | |
| PpdN-5-5 | 5.0 | | |
| PpdNP-3-3 | 2.0 | | |
| Σ | 100.0 | | |

The liquid-crystal medium is introduced into a VA display with TFT addressing. This display has a low addressing voltage and short response times.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I)

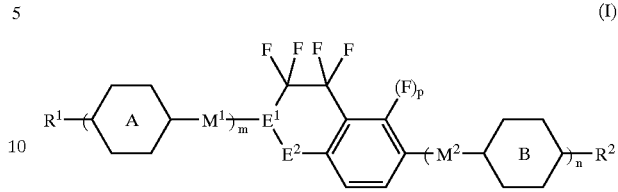

in which $R^1$ and $R^2$, independently of one another, are each H, linear alkyl having from 1 to 12 carbon atoms or linear or branched alkenyl having from 2 to 8 carbon atoms, in which, in said alkyl and alkenyl, a) a non-terminal —$CH_2$— group may be replaced by —O— or —C(=O)O— and/or b) a —$CH_2$— group may be replaced by —C≡C—, cyclopropane-1,2-diyl or cyclobutane-1,3-diyl and/or c) one or more H atoms may be replaced by F, with the proviso that $R^1$ and $R^2$ are not simultaneously H;

$M^1$ and $M^2$, independently of one another, are each —C(=O)O—, —OC(=O)—, —$CH_2$O—, —O$CH_2$—, —C≡C—, —$CH_2CH_2$—, —$(CH_2)_4$—, —$CF_2CF_2$—, —$CF_2$O—, —O$CF_2$— or a single bond;

>$E^1$-$E^2$- is >C=CH— or >CH—$CH_2$—;

m and n, independently of one another, are each zero, 1 or 2, with the proviso that the sum m+n is zero, 1 or 2;

p is zero or 1; and

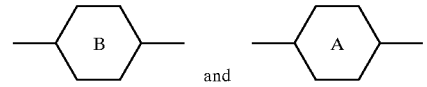

independently of one another, are each phenylene-1,4-diyl, optionally monosubstituted or polysubstituted by F, cyclohexane-1,4-diyl, optionally monosubstituted or disubstituted by F, 1-cyclohexene-1,4-diyl, optionally monosubstituted by F, or 1,3-dioxane-2,5-diyl.

2. A compound according to claim 1, wherein the sum m+n is zero or 1.

3. A compound according to claim 1, wherein $R^1$ and $R^2$, independently of one another, are each H, linear alkyl having from 1 to 5 carbon atoms or linear alkenyl having from 2 to 5 carbon atoms, in which, in said alkyl and alkenyl, a) a non-terminal —$CH_2$— group may be replaced by —O— and/or b) one or more H atoms may be replaced by F, with the proviso that $R^1$ and $R^2$ are not simultaneously H.

4. A compound according to claim 2, wherein $R^1$ and $R^2$, independently of one another, are each H, linear alkyl having from 1 to 5 carbon atoms or linear alkenyl having from 2 to 5 carbon atoms, in which, in said alkyl and alkenyl, a) a non-terminal —$CH_2$— group may be replaced by —O— and/or b) one or more H atoms may be replaced by F, with the proviso that $R^1$ and $R^2$ are not simultaneously H.

5. A compound according to claim 1, wherein >$E^1$-$E^2$- is >CH—$CH_2$—.

6. A compound according to claim 2, wherein >$E^1$-$E^2$- is >CH—$CH_2$—.

7. A compound according to claim 3, wherein >$E^1$-$E^2$- is >CH—$CH_2$—.

8. A compound according to claim 4, wherein >$E^1$-$E^2$- is >CH—$CH_2$—.

9. A compound according to claim 1, wherein >$E^1$-$E^2$- is the >C=CH—.

10. A compound according to claim 2, wherein >$E^1$-$E^2$- is the >C=CH—.

11. A compound according to claim 3, wherein >$E^1$-$E^2$- is the >C=CH—.

12. A compound according to claim 4, wherein >$E^1$-$E^2$- is the >C=CH—.

13. A compound according to claim 1, wherein said compound is of formulae (Ia) to (Ij):

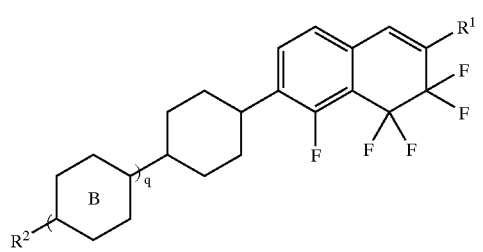
(Ia)

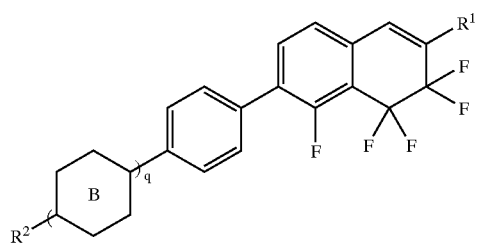
(Ib)

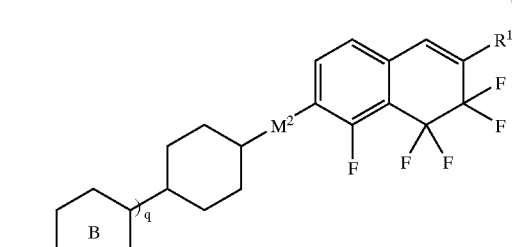
(Ic)

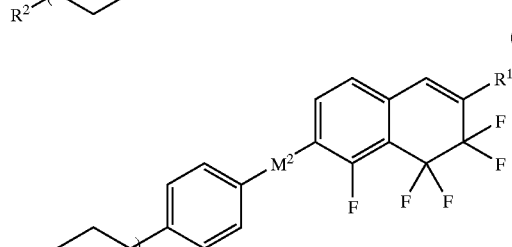
(Id)

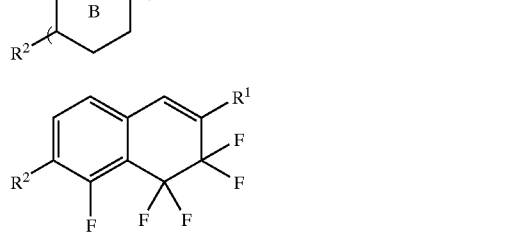
(Ie)

-continued

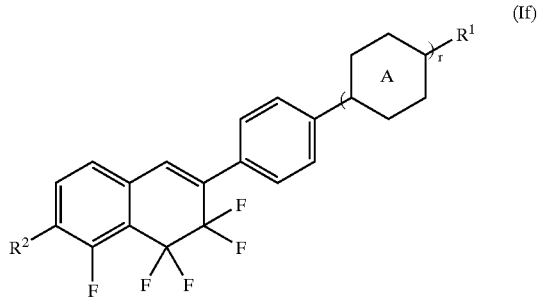
(If)

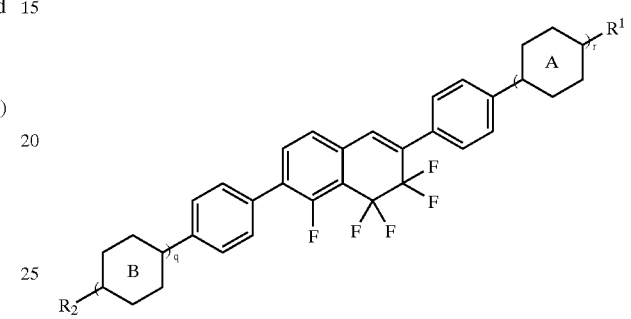
(Ig)

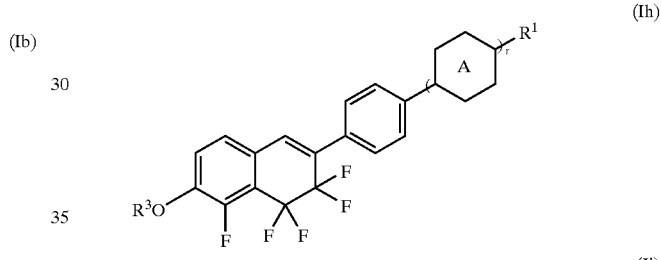
(Ih)

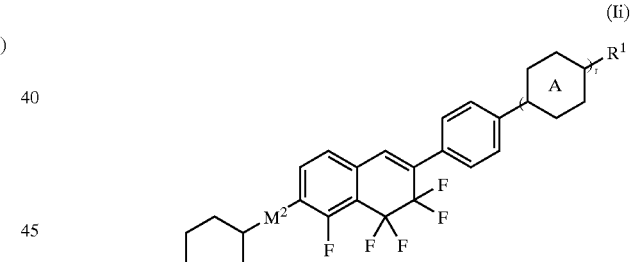
(Ii)

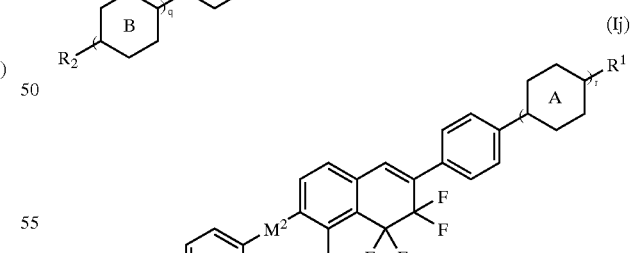
(Ij)

wherein $R^3$ is alkyl having 1 to 12 carbon atoms or alkenyl having 2 to 8 carbon atoms.

q is 0 or 1. and r is 0 or 1, with the proviso that the sum q+r in the compound of formulae (Ig), (Ii) and (Ij) is 0 or 1.

14. A compound according to claim 1, wherein said compound is of formulae

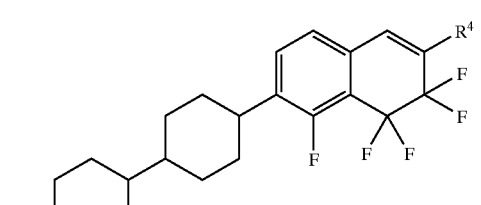
(Ia2)

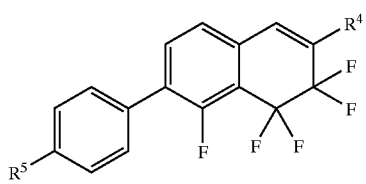
(Ib1)

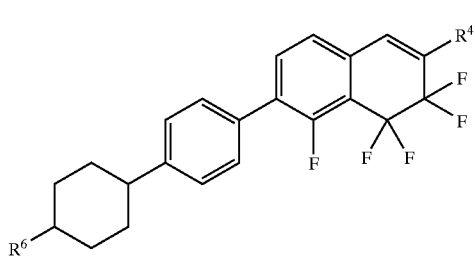
(Ib2)

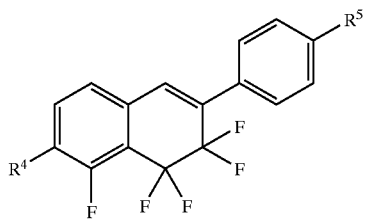
(If1)

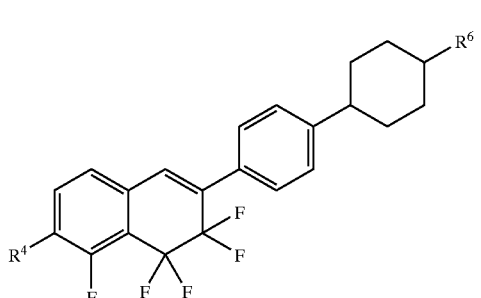
(If2)

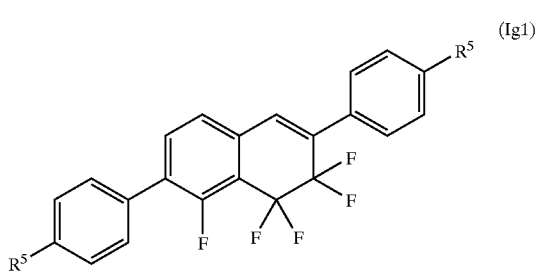
(Ig1)

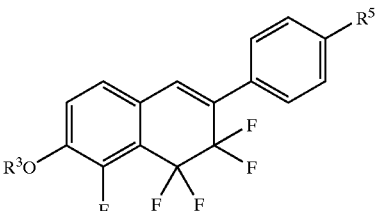
(Ih1)

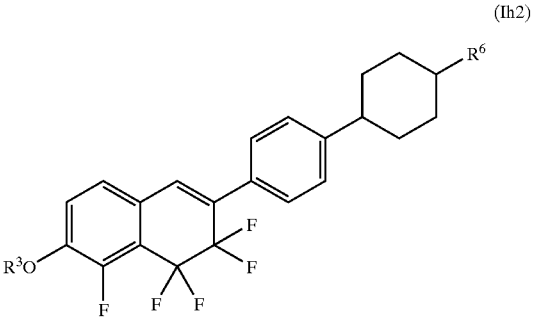
(Ih2)

wherein $R^3$ is alkyl having 1 to 12 carbon atoms or alkenyl having 2 to 8 carbon atoms.

$R^4$ is alkyl having 1 to 6 carbon atoms or alkenyl having 2 to 6 carbon atoms, in each of which a (non-terminal) —$CH_2$— group may also be replaced by —O—.

$R^5$ is alkyl having 1 to 6 carbon atoms or alkenyl having 2 to 6 carbon atoms, in each of which a (non-terminal) —$CH_2$— group may also be replaced by —O—. and $R^6$ is alkyl having from 1 to 6 carbon atoms.

15. In a liquid-crystal medium comprising two or more compounds, the improvement wherein said medium contains at least one compound according to claim 1.

16. A liquid-crystal medium according to claim 15, wherein said medium is nematic or cholesteric.

17. A liquid-crystal medium according to claim 15, wherein the proportion by weight of compounds of formula I is 1 to 80% by weight, based on the weight of the medium as a whole.

18. In a liquid-crystal display containing a liquid-crystal medium, the improvement wherein said medium is in accordance with claim 15.

19. In a method of generating an electro-optical effect using a liquid-crystal display, the improvement wherein said display is in accordance with claim 18.

20. A compound selected from the following formulae:

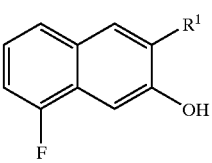
(Z1)

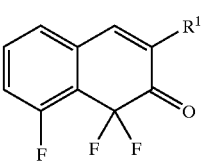
(Z2)

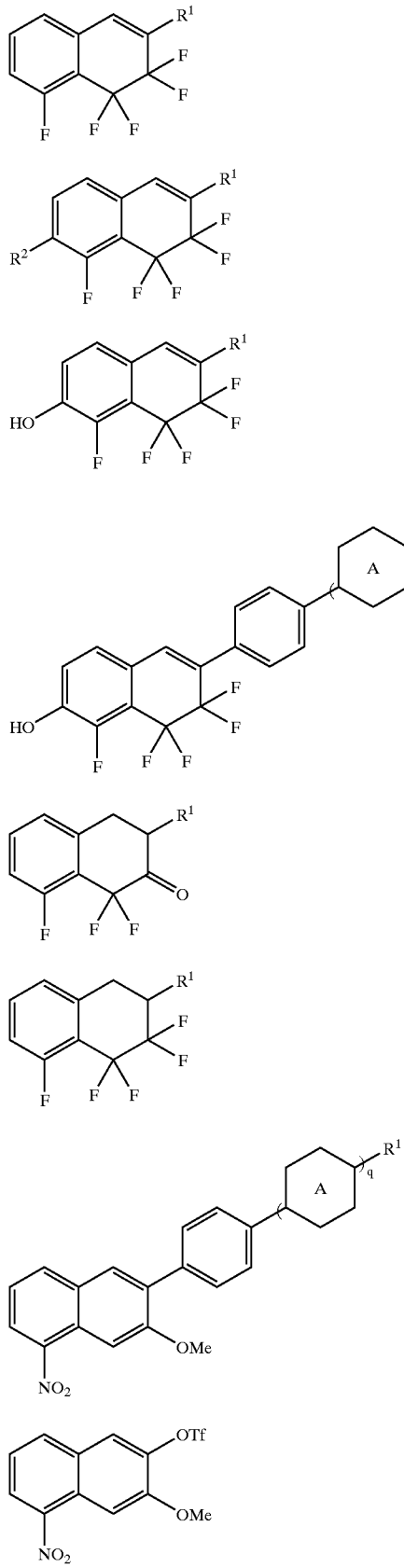
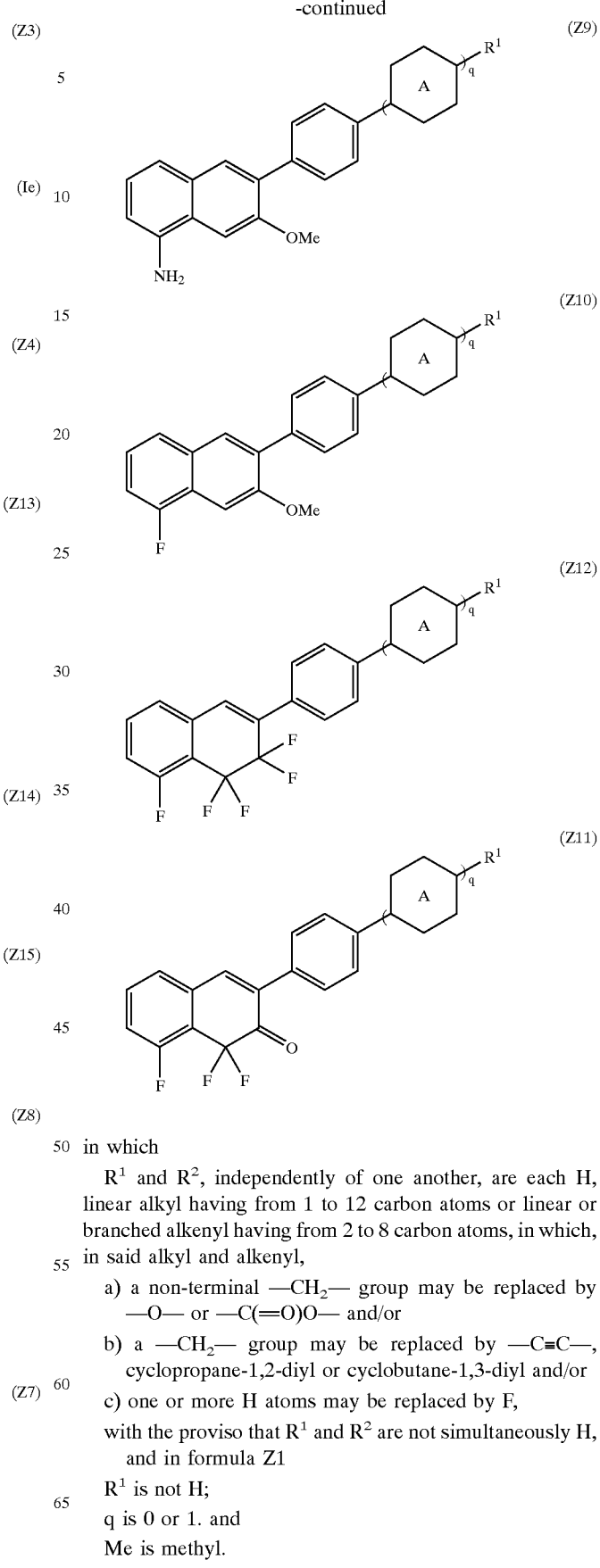

in which

R$^1$ and R$^2$, independently of one another, are each H, linear alkyl having from 1 to 12 carbon atoms or linear or branched alkenyl having from 2 to 8 carbon atoms, in which, in said alkyl and alkenyl, a) a non-terminal —CH$_2$— group may be replaced by —O— or —C(=O)O— and/or b) a —CH$_2$— group may be replaced by —C≡C—, cyclopropane-1,2-diyl or cyclobutane-1,3-diyl and/or c) one or more H atoms may be replaced by F, with the proviso that R$^1$ and R$^2$ are not simultaneously H, and in formula Z1

R$^1$ is not H;

q is 0 or 1. and

Me is methyl.

21. A compound selected from the following formulae:
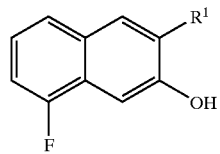
(Z1)
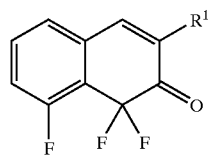
(Z2)
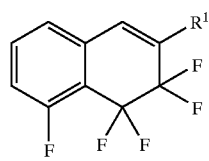
(Z3)
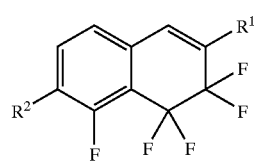
(Ie)
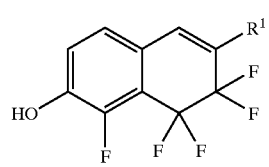
(Z4)
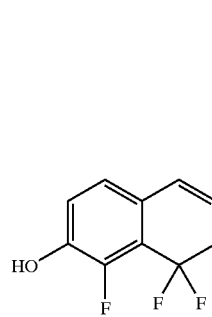
(Z13)
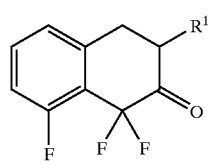
(Z14)
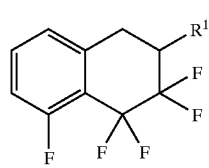
(Z15)
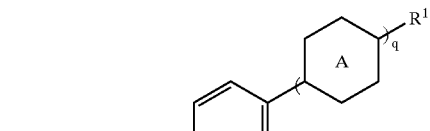
(Z8)
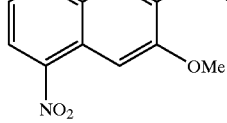
(Z7)
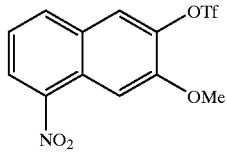
(Z9)
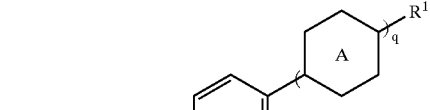
(Z10)
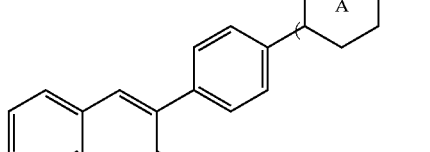
(Z12)
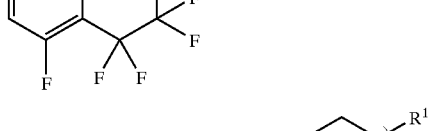
(Z11)

in which

R$^1$ and R$^2$, independently of one another, are each H, linear alkyl having from 1 to 12 carbon atoms or linear or branched alkenyl having from 2 to 8 carbon atoms, in which, in said alkyl and alkenyl, a) a non-terminal —CH$_2$— group may be replaced by —O— or —C(=O)O— and/or b) a —CH$_2$— group may be replaced by —C≡C—, cyclopropane-1,2-diyl or cyclobutane-1,3-diyl and/or c) one or more H atoms may be replaced by F, with the proviso that R$^1$ and R$^2$ are not simultaneously H;

q is 0 or 1. and

Me is methyl.

22. A compound according to claim 1, wherein m is 1 or 2, n is 0, and M$^1$ and M$^2$ are each a single bond.

23. A compound according to claim 1, wherein m is 0, n is 1 or 2, and M$^1$ and M$^2$ are each a single bond.

24. A compound according to claim 1, wherein m is 1 or 2, and

is phenylene-1,4-diyl or cyclohexane-1,4-diyl.

25. A compound according to claim 1, wherein n is 1 or 2, and

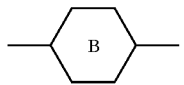

is phenylene-1,4-diyl or cyclohexane-1,4-diyl.

26. A compound according to claim 1, wherein E$^1$-E$^2$- is >C=CH—, p is 1, m is 1 or 2, n is 0, and

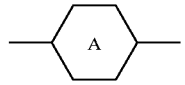

is phenylene-1,4-diyl or cyclohexane-1,4-diyl.

27. A compound according to claim 1, wherein >E$^1$-E$^2$- is >C=CH—, p is 1, m is 0, n is 1 or 2, and

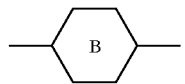

is phenylene-1,4-diyl or cyclohexane-1,4-diyl.

28. A compound according to claim 1, wherein one of R$^1$ and R$^2$ is methyl, ethyl, propyl, butyl, pentyl, hexyl, heptyl, octyl, nonyl, decyl, undecyl, or dodecyl.

29. A compound according to claim 1, wherein one of R$^1$ and R$^2$ is ethoxy, propoxy, butoxy, pentoxy, hexyloxy, heptoxy, octoxy nonoxy, decoxy, undecoxy, or dodecoxy.

30. A compound according to claim 1, wherein one of R$^1$ and R$^2$ is 2-oxapropyl, 2- oxabutyl, 3-oxabutyl, 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-,7-, 8- or 9-oxadecyl.

31. A liquid-crystal medium according to claim 16, wherein the proportion by weight of compounds of formula I is 1 to 80% by weight, based on the liquid-crystal mixture.

32. A liquid-crystal medium according to claim 15, wherein said mixture is a chiral smectic mixture.

33. A liquid-crystal medium according to claim 32, wherein the proportion by weight of compounds of formula I is 3 to 40% by weight, based on the liquid-crystal mixture.

34. A liquid-crystal medium according to claim 32, wherein the proportion by weight of compounds of formula I is 1 to 40% by weight, based on the liquid-crystal mixture.

* * * * *

UNITED STATES PATENT AND TRADEMARK OFFICE
CERTIFICATE OF CORRECTION

PATENT NO.         : 7,014,890 B2
APPLICATION NO. : 10/457022
DATED              : March 21, 2006
INVENTOR(S)        : Bremer et al.

It is certified that error appears in the above-identified patent and that said Letters Patent is hereby corrected as shown below:

Column 56, line 66 reads "q is 0 or 1. and" should read -- q is 0 or 1, and --
Column 58, line 27 reads "2 to 8 carbon atoms." should read -- 2 to 8 carbon atoms, --
Column 58, line 30 reads "replaced by –O–." should read -- replaced by –O–, --
Column 58, line 33 reads "replaced by –O–." should read -- replaced by –O–, --
Column 60, line 66 reads "q is 0 or 1. and" should read -- q is 0 or 1, and --
Column 63, line 14 reads "q is 0 or 1. and" should read -- q is 0 or 1, and --
Column 64, line 24 reads "octoxy nonoxy," should read -- octoxy, nonoxy, --

Signed and Sealed this

Twenty-third Day of January, 2007

JON W. DUDAS
*Director of the United States Patent and Trademark Office*